(12) United States Patent
DeLuca et al.

(10) Patent No.: US 8,575,136 B2
(45) Date of Patent: *Nov. 5, 2013

(54) 2-METHYLENE-1α-HYDROXY-18,19,21-TRINORVITAMIN D₃ ANALOGS AND USES THEREOF

(75) Inventors: Hector F. DeLuca, Deerfield, WI (US); Lori A. Plum, Arena, WI (US); Margaret Clagett-Dame, Deerfield, WI (US); Rafal Barycki, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 395 days.

This patent is subject to a terminal disclaimer.

(21) Appl. No.: 11/697,414

(22) Filed: Apr. 6, 2007

(65) Prior Publication Data

US 2007/0238701 A1    Oct. 11, 2007

Related U.S. Application Data

(60) Provisional application No. 60/744,381, filed on Apr. 6, 2006.

(51) Int. Cl.
*A61K 31/59* (2006.01)
*C07C 401/00* (2006.01)

(52) U.S. Cl.
USPC .......................................... 514/167; 552/653

(58) Field of Classification Search
USPC .................................... 514/167; 552/653
See application file for complete search history.

(56) References Cited

U.S. PATENT DOCUMENTS

| | | | |
|---|---|---|---|
| 4,188,345 A | 2/1980 | DeLuca et al. | |
| 4,411,833 A | 10/1983 | DeLuca et al. | |
| 4,666,634 A | 5/1987 | Miyamoto et al. | |
| 4,970,203 A | 11/1990 | DeLuca et al. | |
| 5,086,191 A | 2/1992 | DeLuca et al. | |
| 5,536,713 A | 7/1996 | DeLuca et al. | |
| 5,585,369 A | 12/1996 | DeLuca et al. | |
| 5,843,928 A * | 12/1998 | Deluca et al. | 514/167 |
| 5,880,114 A | 3/1999 | DeLuca et al. | |
| 5,936,133 A | 8/1999 | DeLuca et al. | |
| 5,945,410 A | 8/1999 | DeLuca et al. | |
| 6,127,559 A | 10/2000 | DeLuca et al. | |
| 6,277,837 B1 | 8/2001 | DeLuca et al. | |
| 6,291,444 B1 | 9/2001 | DeLuca et al. | |
| 6,306,844 B1 | 10/2001 | DeLuca et al. | |
| 6,382,071 B1 | 5/2002 | Bertani et al. | |
| 6,537,981 B2 | 3/2003 | DeLuca et al. | |
| 6,566,352 B1 | 5/2003 | DeLuca et al. | |
| 6,579,861 B2 | 6/2003 | DeLuca et al. | |
| 6,627,622 B2 * | 9/2003 | DeLuca et al. | 514/167 |
| 6,844,330 B2 | 1/2005 | DeLuca et al. | |
| 6,844,331 B2 | 1/2005 | DeLuca et al. | |
| 6,844,332 B2 | 1/2005 | DeLuca et al. | |
| 6,844,457 B2 | 1/2005 | DeLuca et al. | |
| 6,846,811 B2 | 1/2005 | DeLuca et al. | |
| 7,053,075 B2 * | 5/2006 | DeLuca et al. | 514/167 |
| 7,241,749 B2 * | 7/2007 | DeLuca et al. | 514/167 |
| 7,648,972 B2 * | 1/2010 | DeLuca et al. | 514/167 |
| 8,193,169 B2 * | 6/2012 | DeLuca et al. | 514/167 |
| 8,193,170 B2 * | 6/2012 | DeLuca et al. | 514/167 |
| 8,193,171 B2 * | 6/2012 | DeLuca et al. | 514/167 |
| 8,399,439 B2 * | 3/2013 | DeLuca et al. | 514/167 |
| 2003/0158157 A1 | 8/2003 | DeLuca et al. | |
| 2004/0229851 A1 | 11/2004 | DeLuca et al. | |
| 2005/0119242 A1 | 6/2005 | DeLuca et al. | |
| 2007/0191316 A1 | 8/2007 | DeLuca et al. | |
| 2007/0191317 A1 | 8/2007 | DeLuca et al. | |
| 2007/0238701 A1 | 10/2007 | DeLuca et al. | |
| 2012/0283228 A1* | 11/2012 | DeLuca et al. | 514/167 |

FOREIGN PATENT DOCUMENTS

WO    WO 02/058707    8/2002
WO    WO 2005/018648    3/2005

OTHER PUBLICATIONS

Baggiolini et al., "Stereocontrolled Total Synthesis of 1α,25-Dihydroxycholecalciferol and 1α,25-Dihydroxyergocalciferol," Journal of Organic Chemistry, 51, pp. 3098-3108, (1986).

HL-60 Cell Differentiation $EC_{50}$:  $1,25(OH)_2D_3 = 1 \times 10^{-9}$ M
SX-99 = ~$1 \times 10^{-7}$ M Collins et al, "Normal Functional Characteristics of Cultured Human Promyelocytic Leukemia Cells (HL-60) After Inducation of Differentiation by Dimethylsulfoxide," The Journal of Experimental Medicine, vol. 149, pp. 969-974, (1979).
Corey et al, "Computer-Assisted Synthetic Analysis. A Rapid Computer Method for the Semiquantitative Assignment of Conformation of Six-Membered Ring Systems. 1. Derivation of a Preliminary Conformational Description of the Six-Membered Ring," The Journal of Organic Chemistry, vol. 45, No. 5, pp. 757-764, (1980).
Daniewski et al, "A Novel Silylcopper Catalyst for the Reductive Bromination of Hajos Dione. Improved Preparation of a CD Synthon for the Synthesis of Vitamin D," Journal of Organic Chemistry, vol. 66 No. 2, pp. 626-628, (2001).
Fall et al, "Vitamin D Heterocyclic Analogues. Part 1: A Stereoselective Route to CD Systems with Pyrazole Rings in their Side Chains," Tetrahedron Letters 43, pp. 1433-1436, (2002).
Glebocka et al, "New Derivative of 1α,25-Dihydroxy-19-Norvitamin $D_3$ with 3'-Alkoxypropylidene Moiety at C-2: Synthesis, Biological Activity and Conformational Analysis," Journal of Steroid Biochemistry & Molecular Biology, vols. 89-90, pp. 25-30, (2004).
Granja et al, "Studies on the Opening of Dioxanone and Acetal Templates and Application to the Synthesis of 1α,25-Dihydroxyvitamin $D_2$," Journal of Organic Chemistry, vol. 58, pp. 124-131, (1993).
Hanessian et al, "Total Synthesis of (—)-Reserpine Using the Chiron Approach," Journal of Organic Chemistry, vol. 62, pp. 465-473, (1997).
Inhoffen et al, "Studies in the Vitamin D Series, XXI: Hydrindane Compounds from Vitamin $D_3$," Chemische Berichte, vol. 90, pp. 664-673, (1957).
Lythgoe et al, "Calciferol and its Relatives. Part22. A Direct Total Synthesis of Vitamin $D_2$ and Vitamin $D_3$," J. Chem. Soc. Perkin Trans. 1, p. 590, (1978).
Lythgoe, "Synthetic Approaches to Vitamin D and its Relatives," Chem. Soc. Rev. 9, p. 449, (1983).
Mincione et al, "Improved Conversion of Vitamin $D_2$ into the Windaus Ketone and its Regioselective Hydroxylation via Organoboranes at $C_{26}$," Synthetic Communications, vol. 19 Nos. 5-6, pp. 723-735, (1989).
Miyamoto et al, "Synthetic Studies of Vitamin D Analogues. XIV. Synthesis and Calcium Regulating Activity of Vitamin $D_3$ Analogues Bearing a Hydroxyalkoxy Group at the 2β-Position," Chem. Pharm. Bull., vol. 41 No. 6, pp. 1111-1113, (1993).
Nishii et al, "The Development of Vitamin $D_3$ Analogues for the Treatment of Osteoporosis," Osteoporosis Int., Suppl. 1, pp. S190-193, (1993).
Okamura et al, "Vitamin D: Concerning the Relationship Between Molecular Topology and Biological Function," Proc. Nat. Acad. Sci. U.S.A., vol. 71 No. 10, pp. 4194-4197 (1974).
Okano et al, "Regulatory Activities of 2β-(3-Hydroxypropoxy)-1α,25-Dihydroxy-Vitamin $D_3$, A Novel Synthetic Vitamin $D_3$ Derivative, on Calcium Metabolism," Biochemical and Biophysical Research Communications, vol. 163 No. 3, pp. 1444-1449, (1989).
Ono et al, "Efficient Synthesis of 2-Modified 1α,25-Dihydroxy-19-norvitamin $D_3$ with Julia Olefination: High Potency in Induction of Differentiation on HL-60 Cells," Journal of Organic Chemistry, vol. 68, pp. 7407-7415, (2003).
Ostrem et al, "24- and 26-homo-1,25-dihydroxyvitamin $D_3$: Preferential activity in inducing differentiation of human leukemia cells HL-60 in vitro," Proc. Natl. Acad. Sci. USA, vol. 84, pp. 2610-2614, (1987).
Perlman et al, "1α,25-Dihydroxy-19-Nor-Vitainin $D_3$. A Novel Vitamin D-Related Compound with Potential Therapeutic Activity," Tetrahedron Letters, vol. 31 No. 13, pp. 1823-1824, (1990).
Perlman et al, "Novel Synthesis of 19-Nor-Vitamin D Compounds," Tetrahedron Letters, vol. 32 No. 52, pp. 7663-7666, (1991).
Peterson et al, "Studies of the Ketone Obtained from the Ozonolysis of Vitamin D. Molecular Mechanics Calculations for It and Related Hydrindanones," Journal of Organic Chemistry, vol. 51 No. 11, pp. 1948-1954 (1986).
Plum et al, "Biologically Active Noncalcemic Analogs of 1α,25-Dihydroxyvitamin D with an Abbreviated Side Chain Containing No Hydroxyl," PNAS, vol. 101 No. 18, pp. 6900-6904, (2004).
Posner et al, "Stereocontrolled Total Synthesis of Calcitriol Derivatives: 1,25-Dihydroxy-2-(4'-hydroxybutyl)vitamin $D_3$ Analogs of an Osteoporosis Drug," Journal of Organic Chemistry, vol. 59 No. 25, pp. 7855-7861, (1994).

Posner et al, "2-Fluoroalkyl A-Ring Analogs of 1,25-Dihydroxyvitamin $D_3$. Stereocontrolled Total Synthesis via Intramolecular and Intermolecular Diets—Alder Cycloadditions. Preliminary Biological Testing," Journal of Organic Chemistry, vol. 60 No. 14, pp. 4617-4628, (1995).
Rochel et al, "The Crystal Structure of the Nuclear Receptor for Vitamin D Bound to Its Natural Ligand," Molecular Cell, vol. 5, pp. 173-179, (2000).
Sardina et al, "Studies on the Synthesis of Side-Chain Hydroxylated Metabolites of Vitamin D. 2. Stereocontrolled Synthesis of 25-Hydroxyvitamin $D_2$," J. Org. Chem., 51, pp. 1264-1269, (1986).
Sicinski et al, "New 1α,25-Dihydroxy-19-Norvitamin $D_3$ Compounds of High Biological Activity: Synthesis and Biological Evaluation of 2-Hydroxymethyl, 2-Methyl, and 2-Methylene Analogues," Journal of Medical Chemistry, 41, pp. 4662-4674, (1998).
Sicinski et al, "New Highly Calcemic 1α,25-Dihydroxy-19-Norvitamin $D_3$ Compounds with Modified Side Chain: 26,27-Dihomo- and 26,27-Dimethylene Analogs in 20S-Series," Steroids, vol. 67, pp. 247-256, (2002).
Sicinski et al, "2-Ethyl and 2-Ethylidene Analogues of 1α,25-Dihydroxy-19-Norvitamin $D_3$: Synthesis, Conformational Analysis, Biological Activities, and Docking to the Modeled rVDR Ligand Binding Domain," Journal of Medical Chemistry, vol. 45, pp. 3366-3380, (2002).
Tocchini-Valentini et al, "Crystal Structures of the Vitamin D Receptor Complexed to Superagonist 20-epi Ligands," Proc. Natl. Acad. Sci. USA, vol. 98 No. 10, pp. 5491-5496, (2001).
Toh et al, "Studies on a Convergent Route to Side-Chain Analogues of Vitamin D: 25-Hydroxy-23-Oxavitamin $D_3$," J. Org. Chem., 48, 1414, (1983).
Windaus et al, "The Constitution of Vitamin $D_2$ Part II," Annalen der Chemie, 524, pp. 295-299, (1936).
Yoshida et al, "Efficient and Convergent Coupling Route for the Short-step Synthesis of Enantiopure 2α and 2β-Alkylated 1α,25-Dihydroxy-19-norvitamin $D_3$ Analogues," Synlett, No. 8, pp. 1175-1179, (2003).

* cited by examiner

*Primary Examiner* — Sabiha Qazi
(74) *Attorney, Agent, or Firm* — Andrus, Sceales, Starke & Sawall, LLP

(57) ABSTRACT

Compounds of formula I are provided where $X_1$ and $X_2$ are independently selected from H or hydroxy protecting groups. Such compounds are used in preparing pharmaceutical compositions and are useful in treating a variety of biological conditions.

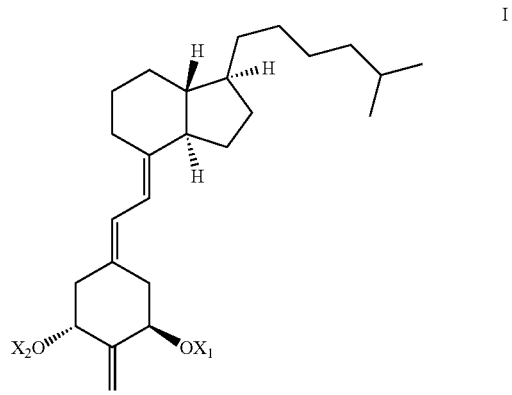

27 Claims, 5 Drawing Sheets

2-METHYLENE-1α-HYDROXY-18,19,21-TRINORVITAMIN D₃ ANALOGS AND USES THEREOF

CROSS-REFERENCE TO RELATED APPLICATION

This application claims the benefit of U.S. Provisional application 60/744,381, filed Apr. 6, 2006, incorporated herein by reference in its entirety for all purposes.

FIELD OF THE INVENTION

This invention relates to vitamin D compounds, and more particularly to 2-methylene-1α-hydroxy-18,19,21-trinorvitamin D3 (SX-99) and to pharmaceutical formulations that include this compound. The invention also relates to the use of 2-Methylene-1α-hydroxy-18,19,21-trinorvitamin D3 or salts thereof in the preparation of medicaments for use in treating various diseases.

BACKGROUND OF THE INVENTION

The natural hormone, 1α,25-dihydroxyvitamin $D_3$ (also referred to as 1α,25-dihydroxycholecalciferol and calcitriol) and its analog in the ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins, and fluorinated analogs. Some of these compounds exhibit an interesting separation of activities in cell differentiation and calcium regulation. This difference in activity is useful in the treatment of a variety of diseases as established in the art, such as renal osteodystrophy, vitamin D-resistant rickets, osteoporosis, psoriasis, and certain malignancies (see for example, Zemplar, Calcipotriol, MC-903, Dovonex, 22-oxa-1α, 25-$(OH)_2D_3$) Slatopolsky, E., Finch, J., Ritter, C., Denda, M., Morrissey, J., Brown, A. & DeLuca, H. (1995) Am. J. Kidney Dis. 26, 852-860; Kubodera, N., Sato, K. & Nishii, Y. (1997) in Vitamin D, eds. Feldman, D., Glorieux, F. H. & Pike, J. W. (Academic, N.Y.), Vol. 63, pp. 1071-1086; Calverley, M. J. (1987) Tetrahedron Lett. 43, 4609-4619; Uskokovic, M. R., Studzinski, G. P. & Reddy, S. G. (1997) in Vitamin D, eds. Feldman, D., Glorieux, F. H. & Pike, J. W. (Academic, N.Y.), Vol. 62, pp. 1045-1070; Kensler, T. W., Dolan, P. M., Gange, S. J., Lee, J.-K., Wang, Q. & Posner, G. H. (2000) Carcinogenesis 21, 1341-1345; Binderup, L., Binderup, E. & Godfredsen, W. O. (1997) in Vitamin D, eds. Feldman, D., Glorieux, F. H. & Pike, J. W. (Academic, N.Y.), Vol. 61, pp. 1027-1043; Jones, G. (1997) in Vitamin D, eds. Feldman, D., Glorieux, F. H. & Pike, J. W. (Academic, N.Y.), Vol. 58, pp. 973-994; Brown, A. J. & Slatopolsky, E. (1997) in Vitamin D, eds. Feldman, D., Glorieux, F. H. & Pike, J. W. (Academic, N.Y.), Vol. 59, pp. 995-1009; Shankar, V. N., Propp, A. E., Schroeder, N. S., Surber, B. W., Makin, H. L. J. & Jones, G. (2001) Arch. Biochem. Biophys. 387, 297-306. All these references are incorporated herein by reference for all purposes.

As discussed above, renal osteodystrophy is a bone disease that occurs when the kidneys fail to maintain the proper levels of calcium and phosphorus in the blood. Renal osteodystrophy is a common problem in people with kidney disease and affects 90 percent of dialysis patients.

Renal osteodystrophy is most serious in children because their bones are still growing. The condition slows bone growth and causes deformities. One such deformity occurs when the legs bend inward toward each other or outward away from each other; this deformity is referred to as "renal rickets." Another important consequence is short stature. Symptoms can be seen in growing children with renal disease even before they start dialysis.

The bone changes from renal osteodystrophy can begin many years before symptoms appear in adults with kidney disease. The symptoms of renal osteodystrophy are not usually seen in adults until they have been on dialysis for several years. Older patients and women who have gone through menopause are at greater risk for this disease because they're already vulnerable to osteoporosis, even without kidney disease. If left untreated, the bones gradually become thin and weak, and a person with renal osteodystrophy begins to experience bone and joint pain and an increased risk of bone fractures.

In healthy adults, bone tissue is continually being remodeled and rebuilt. The kidneys play an important role in maintaining healthy bone mass and structure because it balances calcium and phosphorus levels in the blood. If calcium levels in the blood become too low, the parathyroid glands release parathyroid hormone (PTH). This hormone draws calcium from the bones to raise blood calcium levels. Too much PTH in the blood causes disturbances in calcium and phosphorus homeostasis. This in turn removes too much calcium from the bones; over time, the constant removal of calcium weakens the bones.

Secondary hyperparathyroidism is characterized by an elevation PTH associated with inadequate levels of active vitamin D hormone. Typically, Vitamin D requires two sequential hydroxylations in the liver and the kidney to bind to activate the Vitamin D receptor (VDR). The endogenous VDR activator, calcitriol [1,25$(OH)_2$ $D_3$] is a hormone that binds to VDRs that are present in the parathyroid gland, intestine, kidney, and bone to maintain parathyroid function and calcium and phosphorus homeostasis, and to VDRs found in many other tissues, including prostate, endothelium and immune cells. Phosphorus also helps regulate calcium levels in the bones. Healthy kidneys remove excess phosphorus from the blood. When the kidneys stop working normally, phosphorus levels in the blood can become too high, leading to lower levels of calcium in the blood and resulting in the loss of calcium from the bones.

Healthy kidneys produce calcitriol to help the body absorb dietary calcium into the blood and the bones. If calcitriol levels drop too low, PTH levels increase, and calcium is removed from the bones. Calcitriol and PTH work together to keep calcium balance normal and bones healthy. In a patient with kidney failure, the kidneys stop making calcitriol, dietary calcium is not absorbed and calcium is removed from the bones.

Controlling PTH levels prevents calcium from being withdrawn from the bones. Usually, overactive parathyroid glands are controllable with a change in diet, dialysis treatment, or medication. The drug cinacalcet hydrochloride (Sensipar), approved by the Food and Drug Administration in 2004, lowers PTH levels by binding to the calcium receptor that controls PTH release. If PTH levels cannot be controlled, the parathyroid glands may need to be removed surgically. Other treatments for the condition include taking synthetic calcitriol as a pill or in an injectable form.

Renal osteodystrophy can also be treated with changes in diet. Reducing dietary intake of phosphorus is one of the most important steps in preventing bone disease. Often, medications such as calcium carbonate (Tums), calcium acetate (PhosLo), sevelamer hydrochloride (Renagel), or lanthanum carbonate (Fosrenol) are prescribed with meals and snacks to bind phosphorus in the bowel, which decreases the absorption of phosphorus into the blood.

Other treatment choices for renal osteodystrophy include Paricalcitol, the active ingredient of Zemplar (paracalcitol injection, USP), which is a synthetic, biologically active vitamin D analog of calcitriol with modifications to the side chain and the A (19-nor) ring. Preclinical and in vitro studies have demonstrated that paricalcitol's actions are mediated through binding to the VDR, resulting in the selective activation of Vitamin D response pathways. Calcitriol and paricalcitol have been shown to reduce parathyroid hormone levels by inhibiting PTH synthesis and secretion.

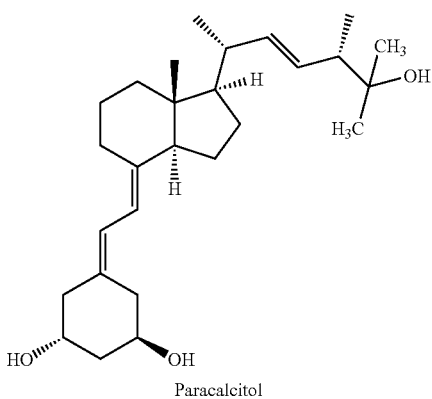 [SMILES: C[C@H](/C=C/[C@H](C)C(C)(C)O)[C@H]1CC[C@H]2/C(=C/C=C3C[C@@H](O)C[C@H](O)C3)CCC[C@]12C]

Paracalcitol

The structure of 1α,25-dihydroxyvitamin $D_3$ and the numbering system used to denote the carbon atoms in this compound are shown below.

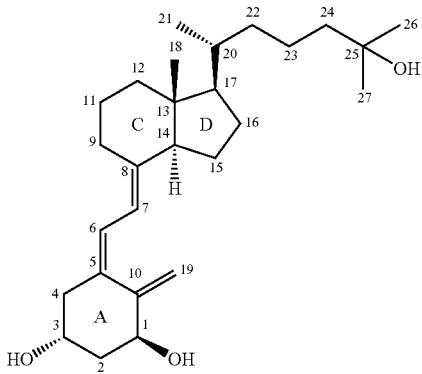

1α,25-Dihydroxyvitamin $D_3$=1α,25-Dihydroxycholecalciferol=Calcitriol

Typically, the class of vitamin D analogs such as 19-nor-vitamin D compounds is characterized by the absence of carbon 19 from the A-ring exocyclic methylene group, typical of the vitamin D system. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. application Ser. Nos. 11/669,029 and 11/669,053 filed on Jan. 30, 2007, (20R,25S)-2-Methylene-19,26-dinor-1α,25-dihydroxyvitamin D3 (NEL) and (20S,25S)-2-Methylene-19,26-dinor-1α,25-dihydroxyvitamin D3 (RAK) have been described and examined by DeLuca et al. as potential drugs for treatment of renal osteodystrophy. In U.S. Pat. No. 4,666,634, 2β-hydroxy and alkoxy (e.g., ED-71) analogs of 1α,25-dihydroxyvitamin $D_3$ have been described and examined by the Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

Various 2-substituted analogs of 1α,25-dihydroxy-19-nor-vitamin $D_3$ have also been synthesized, i.e. compounds substituted at the 2-position with hydroxy or alkoxy groups (DeLuca et al., U.S. Pat. No. 5,536,713), with 2-alkyl groups (DeLuca et al., U.S. Pat. No. 5,945,410), and with 2-alkylidene groups (DeLuca et al., U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs that are characterized by the presence of a methylene substituent at carbon 2 (C-2), a hydroxyl group at carbon 1 (C-1), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-(20S)-homopregnacalciferol is described in U.S. Pat. No. 6,579,861 and 1α-hydroxy-2-methylene-19-nor-substituted bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents. Other 19-nor compounds are disclosed in U.S. patent application Ser. Nos. 10/996,642 and 10/997,698. All these patents and patent applications are incorporated herein by reference for all purposes.

Since the currently available treatments, including compounds and formulations described above have various limitations to a greater or lesser extent, new compounds and pharmaceutical formulations are desirable that continue to decrease the calcemic effect while retaining the ability to suppress PTH.

SUMMARY OF THE INVENTION

The invention generally provides 2-methylene-1α-hydroxy-18,19,21-trinorvitamin D3 (SX-99) and related compounds, pharmaceutical formulations that include SX-99 and the use of this compound in the preparation of medicaments for use in treating various disease states.

Therefore, in one aspect, the invention provides a compound having the formula I as shown below:

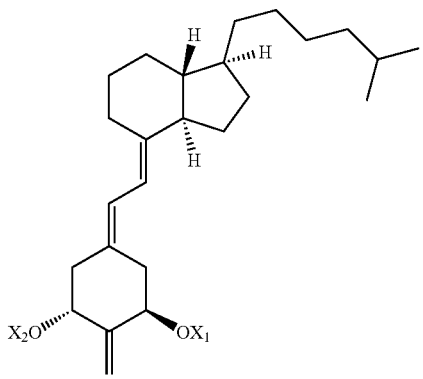

I where $X_1$ and $X_2$ are the same or different and are independently selected from H or hydroxy-protecting groups. In some embodiments, $X_1$ and $X_2$ are hydroxy protecting groups such as silyl ether groups, alkyl ether groups, alkoxyalkyl ether group, acetal groups and ester groups. In some such embodiments, $X_1$ and $X_2$ are t-butyldimethylsilyl ether group (TBDMS), trimethylsilyl ether group (TMS), triethylsilyl ether group (TES), Triisopropylsilyl ether group (TIPS), t-butyldiphenylsilyl ether group (TBDPS), tetrahydropyran group (THP), methoxyethoxymethyl group (MEM), methoxymethyl group (MOM), benzyl ether group, t-butyl ether group, N-phthalimido acetal group (Nphth), isopropylidene, trimethoxy butane, 2,4-dimethylpentan-3-yloxycarbonyl group (Doc). Various other hydroxy protecting groups are known to one of ordinary skill in the art, for example see Jarowicki et al, J. Chem. Soc., Perkin Trans. 1, 1998, 4005-4037, which is incorporated herein by reference for all purposes.

In other embodiments, $X_1$ and $X_2$ are H such that the compound is 2-methylene-1α-hydroxy-18,19,21-trinorvitamin D3 (SX-99) having the formula II as shown below:

II

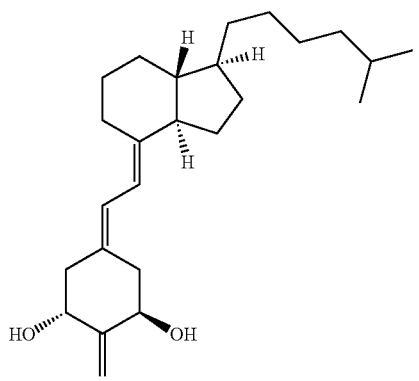

Another embodiment of the present invention provides a pharmaceutical composition, comprising an effective amount of the compound of formula I or II and a pharmaceutically acceptable carrier. In this pharmaceutical composition the effective amount comprises from about 0.01 µg to about 1 mg of the compound per gram of the composition. More preferably, the effective amount comprises from about 0.1 µg to about 500 µg of the compound per gram of the composition.

In certain embodiments, the present invention provides a method of treating a subject suffering from a biological condition, comprising administering an effective amount of the compound of formula I or II to the subject, wherein the biological condition is selected from metabolic bone diseases such as osteomalacia and vitamin D resistant rickets; psoriasis; leukemia; colon cancer; breast cancer; prostate cancer; skin cancer; lung cancer; multiple sclerosis; lupus; diabetes mellitus; host versus graft reaction; rejection of organ transplants; an inflammatory disease selected from rheumatoid arthritis, asthma, or inflammatory bowel diseases such as celiac disease, ulcerative colitis and Crohn's disease; a skin condition selected from wrinkles, lack of adequate skin firmness, lack of adequate dermal hydration, or insufficient sebum secretion; renal osteodystrophy; osteopenia; or osteoporosis particularly senile osteoporosis, postmenopausal osteoporosis, steroid-induced osteoporosis and low bone turnover osteoporosis. In an exemplary embodiment, the biological condition is renal osteodystrophy, vitamin D-resistant rickets, osteoporosis or psoriatic arthritis. In another exemplary embodiment, the biological condition is selected from leukemia, colon cancer, breast cancer, skin cancer, lung cancer, or prostate cancer. In yet another exemplary embodiment, the biological condition is selected from multiple sclerosis, lupus, diabetes mellitus, host versus graft reaction, or rejection of organ transplants. In still other exemplary embodiment, the biological condition is selected from rheumatoid arthritis, asthma, or inflammatory bowel diseases selected from celiac disease, ulcerative colitis and Crohn's disease. In yet other exemplary embodiment, the biological condition is selected from wrinkles, lack of adequate skin firmness, lack of adequate dermal hydration, or insufficient sebum secretion.

Also preferably, in this embodiment, the effective amount of the compound is administered orally, parenterally, transdermally, nasally, rectally, sublingually, or topically to the subject. Yet more preferably, the effective amount of the compound is administered intraperitoneally. In this embodiment, the compound is administered in a dosage of from 0.01 µg per day to 1 mg per day.

Another aspect of the invention provides the use of the compound of formula I in the preparation of a medicament for the treatment of a biological condition selected from metabolic bone diseases such as osteomalacia and vitamin D resistant rickets; psoriasis; leukemia; colon cancer; breast cancer; prostate cancer; skin cancer; lung cancer; multiple sclerosis; lupus; diabetes mellitus; host versus graft reaction; rejection of organ transplants; an inflammatory disease selected from rheumatoid arthritis, asthma, or inflammatory bowel diseases such as celiac disease, ulcerative colitis and Crohn's disease; a skin condition selected from wrinkles, lack of adequate skin firmness, lack of adequate dermal hydration, or insufficient sebum secretion; renal osteodystrophy; osteopenia; or osteoporosis, particularly senile osteoporosis, postmenopausal osteoporosis, steroid-induced osteoporosis and low bone turnover osteoporosis.

Yet another preferred embodiment of the present invention provides the compound having the formula II

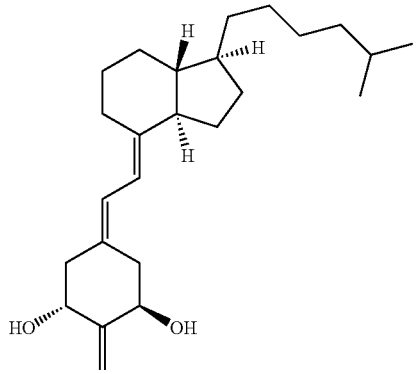

II

The invention also teaches a pharmaceutical composition having an effective amount of the compound of formula II and a pharmaceutically acceptable carrier.

Another aspect of the invention provides the use of the compound of formula II in the preparation of a medicament for the treatment of a biological condition selected from metabolic bone diseases such as osteomalacia and vitamin D resistant rickets; psoriasis; leukemia; colon cancer; breast cancer; prostate cancer; skin cancer; lung cancer; multiple sclerosis; lupus; diabetes mellitus; host versus graft reaction; rejection of organ transplants; an inflammatory disease selected from rheumatoid arthritis, asthma, or inflammatory bowel diseases such as celiac disease, ulcerative colitis and Crohn's disease; a skin condition selected from wrinkles, lack of adequate skin firmness, lack of adequate dermal hydration, or insufficient sebum secretion; renal osteodystrophy; osteopenia; or osteoporosis particularly senile osteoporosis, postmenopausal osteoporosis, steroid-induced osteoporosis and low bone turnover osteoporosis.

Further objects, features and advantages of the invention will be apparent from the following detailed description, drawings and appended claims.

BRIEF DESCRIPTION OF THE DRAWINGS

FIG. 1 is a graph comparing the relative activity of SX-99 and 1,25$(OH)_2D_3$ to compete for binding with [$^3$H]-1,25-$(OH)_2$-$D_3$ to the full-length recombinant rat vitamin D receptor.

FIG. 2 is a bar graph comparing the bone calcium mobilization activity of SX-99 with that of 1,25$(OH)_2D_3$.

FIG. 3 is a bar graph comparing the intestinal calcium transport activity of SX-99 with that of 1,25$(OH)_2D_3$.

FIG. 4 is a graph comparing the percent HL-60 cell differentiation as a function of the concentration of SX-99 with that of 1,25$(OH)_2D_3$.

FIG. 5 is a graph comparing the in vitro transcription activity of SX-99 with that of 1,25$(OH)_2D_3$.

DETAILED DESCRIPTION OF THE INVENTION

Figure 1:
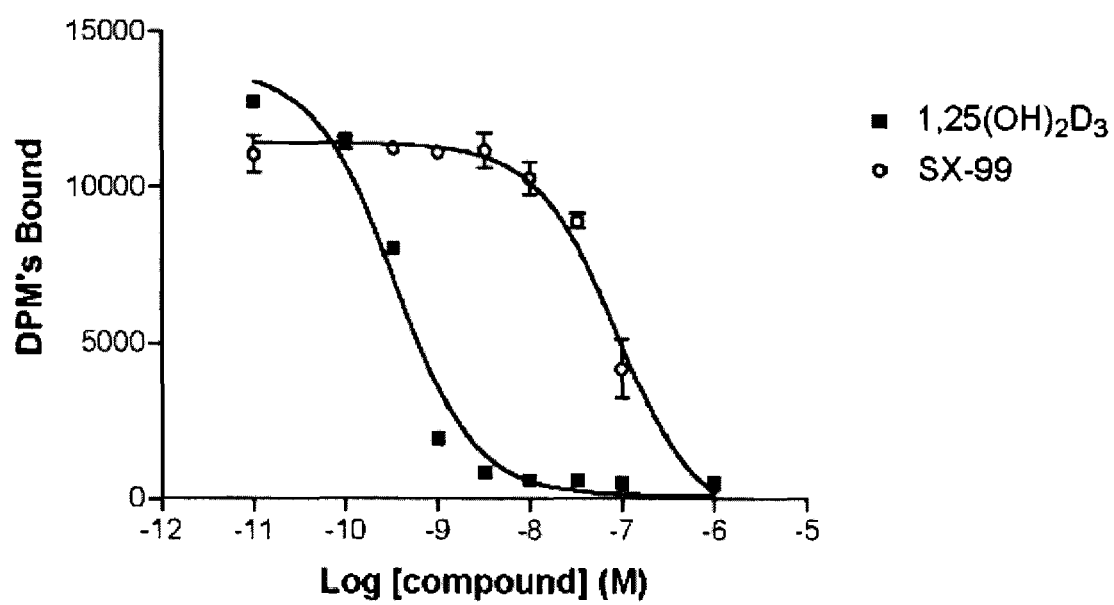
FIGS. 1-5 illustrate various biological activities of 2-methylene-1α-hydroxy-18,19,21-trinorvitamin D3 (referred to as "SX-99" in the Figures) compared with those of the native hormone 1α,25-dihydroxyvitamin $D_3$ (referred to as "1, 25$(OH)_2D_3$" in the Figures).

Generally, the invention provides a compound having the formula I as shown below:

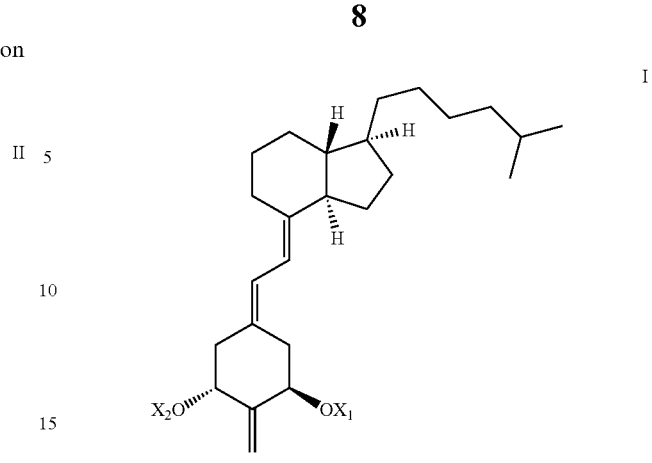

I where $X_1$ and $X_2$ are the same or different and are independently selected from H or hydroxy-protecting groups. In some embodiments, $X_1$ and $X_2$ are hydroxy protecting groups such as silyl ether groups, alkyl ether groups, alkoxyalkyl ether group, acetal groups and ester groups. In some such embodiments, $X_1$ and $X_2$ are t-butyldimethylsilyl ether group (TBDMS), trimethylsilyl ether group (TMS), triethylsilyl ether group (TES), Triisopropylsilyl ether group (TIPS), t-butyldiphenylsilyl ether group (TBDPS), tetrahydropyran group (THP), methoxyethoxymethyl group (MEM), methoxymethyl group (MOM), benzyl ether group, t-butyl ether group, N-phthalimido acetal group (Nphth), isopropylidene, trimethoxy butane, 2,4-dimethylpentan-3-yloxycarbonyl group (Doc). As discussed above, various other hydroxy protecting groups are known to one of ordinary skill in the art, for example see Jarowicki et al, J. Chem. Soc., Perkin Trans. 1, 1998, 4005-4037, which is incorporated herein by reference for all purposes.

Also as used herein, the term "hydroxy-protecting group" signifies any group commonly used for the temporary protection of the hydroxy (—OH) functional group, such as, but not limited to, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. An extensive list of protecting groups for the hydroxy functionality is found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for all purposes as if fully set forth herein.

A "protected hydroxy" group is a hydroxy group derivatized or protected by any of the above groups commonly used for the temporary or permanent protection of hydroxy functional groups, e.g., the silyl, alkoxyalkyl, acyl or alkoxycarbonyl groups, as previously defined.

In other embodiments, $X_1$ and $X_2$ are H such that the compound is 2-methylene-1α-hydroxy-18,19,21-trinorvitamin D3 (SX-99) having the formula II as shown below:

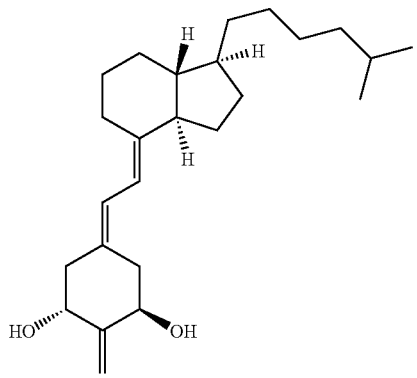

II

The compound of formula II (SX-99) exhibits a desired, and highly advantageous, pattern of biological activity. This compound is characterized by relatively high binding to vitamin D receptors, and significant intestinal calcium transport activity, as compared to that of 1α,25-dihydroxyvitamin $D_3$, and has good ability to mobilize calcium from bone, as compared to 1,25-dihydroxyvitamin $D_3$. Hence, this compound can be characterized as having significant calcemic activity. Thus, it is useful as a therapy for treatment of metabolic bone diseases.

The compound of the invention is also especially suited for treatment and prophylaxis of human disorders which are characterized by an imbalance in the immune system, e.g. in autoimmune diseases, including multiple sclerosis, lupus, diabetes mellitus, host versus graft reaction, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which are treated with the compound of the invention.

The above compound is also characterized by relatively high cell differentiation activity. Thus, this compound also provides a therapeutic agent for the treatment of psoriasis, or as an anti-cancer agent, especially against leukemia, colon cancer, breast cancer, skin cancer, lung cancer, and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

The compounds of the invention are used to prepare pharmaceutical formulations or medicaments that include a compound of the invention in combination with a pharmaceutically acceptable carrier. Such pharmaceutical formulations and medicaments are used to treat various biological disorders such as those described herein. Methods for treating such disorders typically include administering an effective amount of the compound or an appropriate amount of a pharmaceutical formulation or a medicament that includes the compound to a subject suffering from the biological disorder. In some embodiments, the subject is a mammal. In some such embodiments, the mammal is selected from a rodent, a primate, a bovine, an equine, a canine, a feline, an ursine, a porcine, a rabbit, or a guinea pig. In some such embodiments, the mammal is a rat or is a mouse. In some embodiments, the subject is a primate such as, in some embodiments, a human.

The compounds is present in a composition to treat the above-noted diseases and disorders in an amount from about 0.01 μg/gm to about 1 mg/gm of the composition, preferably from about 0.1 μg/gm to about 500 μg/gm of the composition, and is administered topically, transdermally, orally, or parenterally in dosages of from about 0.01 μg/day to about 1 mg/day, preferably from about 0.1 μg/day to about 500 μg/day.

In one embodiment, the invention provides compounds II as shown below:

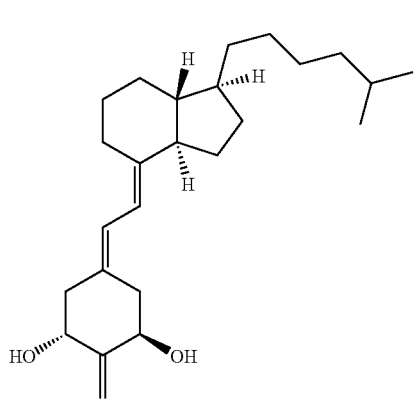

II

In a preferred embodiment, 2-methylene-1α-hydroxy-18,19,21-trinorvitamin D3 (SX-99) was synthesized, and tested, and is useful in treating a variety of biological conditions as described herein.

Preparation of 2-methylene-1α-hydroxy-18,19,21-trinorvitamin D3 (SX-99) can be accomplished by condensing an appropriate bicyclic Windaus-Grundmann type ketone (III) with the allylic phosphine oxide IV followed by deprotection (removal of the $Y_1$, and $Y_2$ groups). Other compounds of the present invention are similarly synthesized.

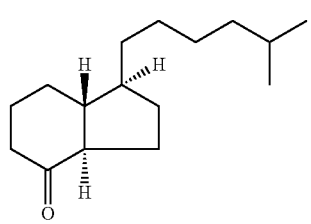

III

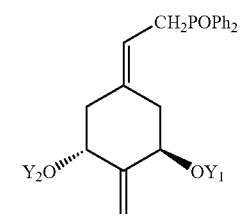

IV

In phosphine oxide IV, $Y_1$ and $Y_2$ are preferably hydroxy-protecting groups such as silyl protecting groups. In a preferred embodiment, the triethylsilyl group (TES) and t-butyldimethylsilyl (TBDMS) group are examples of a particularly useful hydroxy-protecting groups. The process described above represents an application of the convergent synthesis concept, which has been applied effectively to the preparation of numerous vitamin D compounds (see Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713; and DeLuca et al., U.S. Pat. No. 5,843,928 all of which are hereby incorporated by reference in their entirety and for all purposes as if fully set forth herein).

variety of phosphonium compounds is used in place of the $MePh_3P^+ Br^-$ used to convert ketone B to alkene C. Examples of such compounds include $EtPh_3P^+ Br^-$, $PrPh_3P^+ Br^-$, and compounds generally prepared by reaction of triphenylphosphine with an alkyl halide, an alkenyl halide, a protected-hydroxyalkyl halide, and a protected hydroxyalkenyl halide. Alkenes prepared using this procedure may then be carried through to prepare a phosphine oxide in an analogous manner to that used to prepare phosphine oxide H in Scheme I. Alternatively, an alkene analogous to compound C of Scheme I is reduced with $(Ph_3P)_3RhCl$ and $H_2$ to provide other vitamin D analogs. See U.S. Pat. No. 5,945,410 and Sicinski, R. R. et al., J. Med. Chem., 41, 4662-4674 (1998) both of which are hereby incorporated by reference in their entireties and for all purposes. Therefore, the procedure for forming the phosphine oxide shown in Scheme I is used to prepare a wide variety of vitamin D analogs in addition to the compound of the present invention.

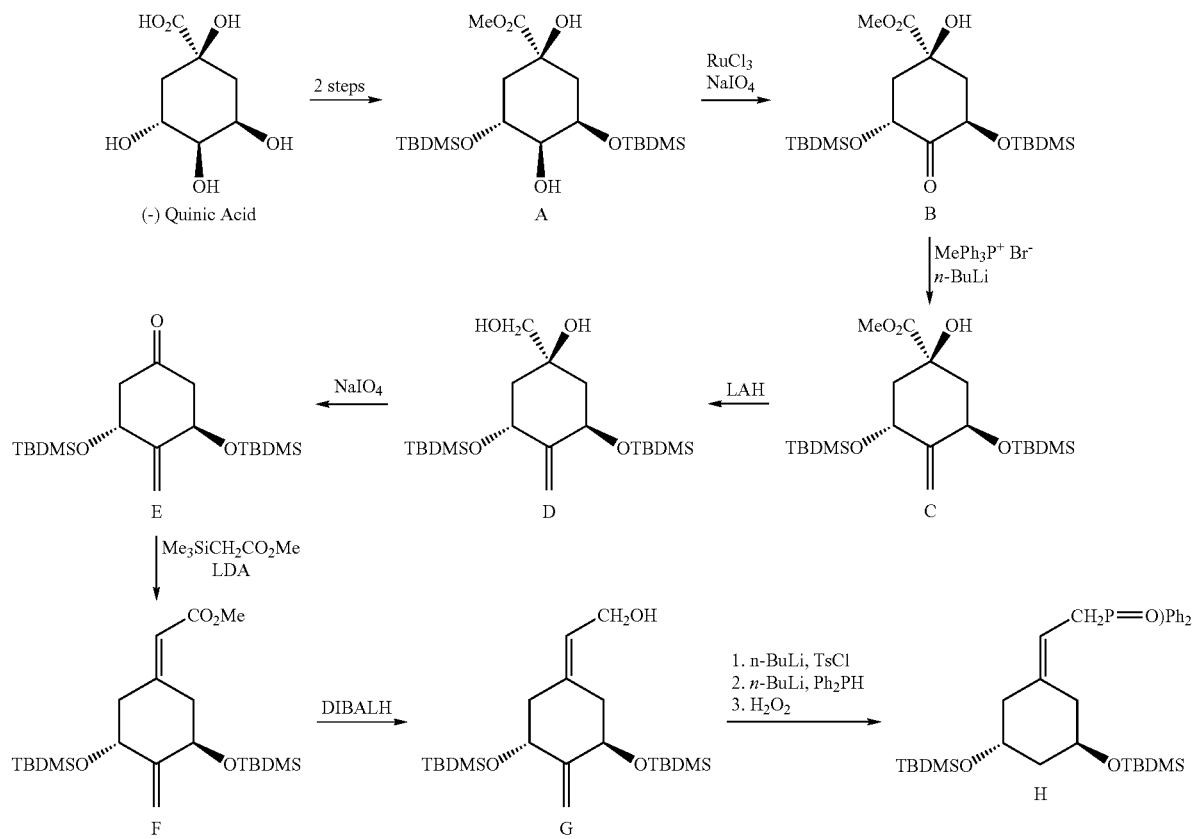

Scheme I

Phosphine oxide IV is a convenient reagent that can be used to prepare a large number of 19-nor vitamin D compounds and is prepared according to the procedures described by Sicinski et al., J. Med. Chem., 41, 4662 (1998), DeLuca et al., U.S. Pat. No. 5,843,928; Perlman et al., Tetrahedron Lett. 32, 7663 (1991); and DeLuca et al., U.S. Pat. No. 5,086,191. Scheme I shows the general procedure for synthesizing phosphine oxide IV as outlined in U.S. Pat. No. 5,843,928 which is hereby incorporated by reference in its entirety as if fully set forth herein. Modification of the method shown in Scheme I is used to produce a large number of vitamin D analogs as will be apparent to those skilled in the art. For example, a wide Hydraindanones of structure III can prepared by known methods or adapted methods as will be readily apparent to one of skill in the art and described herein. Specific examples of some important bicyclic ketones used to synthesize vitamin D analogs are those described in Mincione et al., Synth. Commun 19, 723, (1989); and Peterson et al., J. Org. Chem. 51, 1948, (1986).

In one preferred embodiment, ketone III (19) and compound of Formula II (SX-99) (22) were prepared by the following Schemes II and III, as shown below:

Scheme II

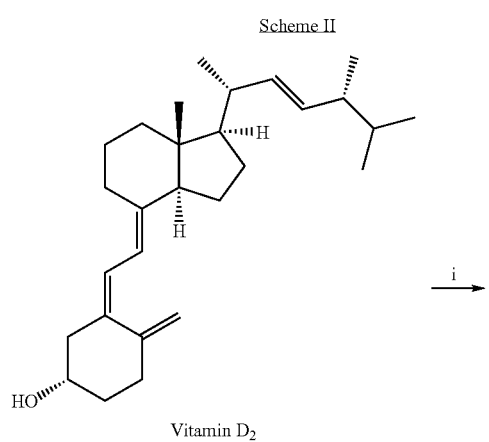

Vitamin D$_2$ $\xrightarrow{i}$

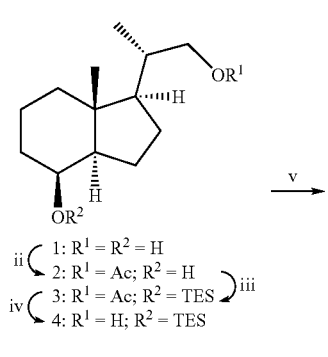

ii ( 1: R$^1$ = R$^2$ = H
ii ( 2: R$^1$ = Ac; R$^2$ = H ) iii
iv ( 3: R$^1$ = Ac; R$^2$ = TES ) iii
iv ( 4: R$^1$ = H; R$^2$ = TES $\xrightarrow{v}$

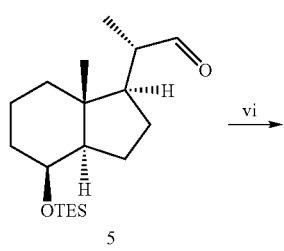
5

$\xrightarrow{vi}$

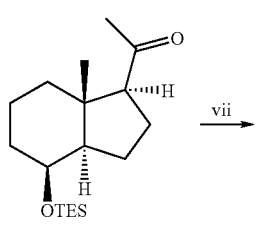
6

$\xrightarrow{vii}$

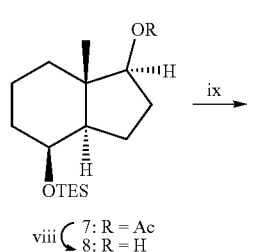

viii ( 7: R = Ac
     ( 8: R = H $\xrightarrow{ix}$

-continued

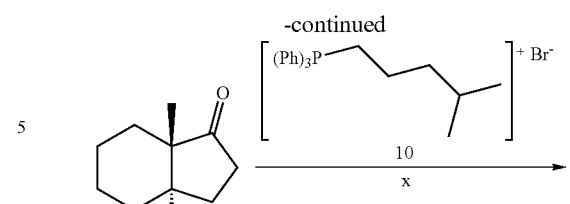
9

$\xrightarrow{x}$

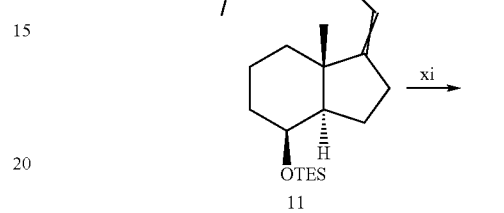
11

$\xrightarrow{xi}$

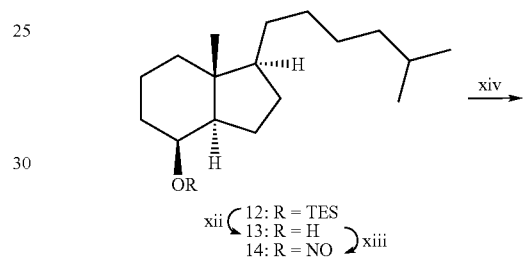

xii ( 12: R = TES
xii ( 13: R = H   ) xiii
     ( 14: R = NO $\xrightarrow{xiv}$

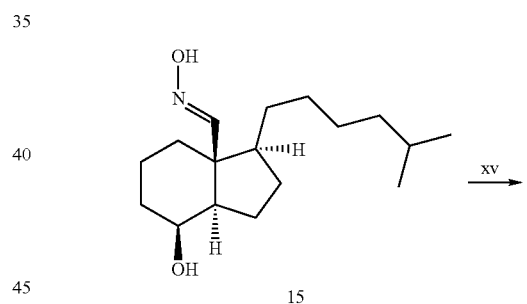
15

$\xrightarrow{xv}$

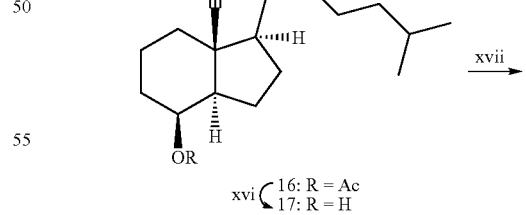

xvi ( 16: R = Ac
    ( 17: R = H $\xrightarrow{xvii}$

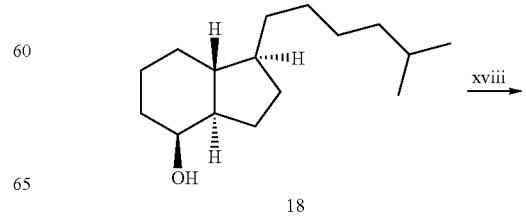
18

$\xrightarrow{xviii}$

Scheme IV:

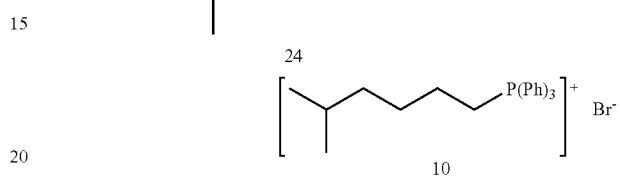

(i) TsCl, Et$_3$N, DMAP, CH$_2$Cl$_2$, 96%. (ii) LiBr, DMF, 55%. (iii) Ph$_3$P, PhMe, 81%.

Following examples illustrate synthesis and biological activity of the compounds provided in the present invention. These Examples are for illustration purposes only and should not be deemed to limit the scope of the invention.

Example I

SX-99 Synthesis

Des-A,B-23,24-dinorcholane-8β,22-diol (1)

A solution of vitamin D$_2$ (5 g; 12.7 mmol) in methanol (400 mL) and pyridine (5 mL) was cooled to −78° C. while purging with argon. The argon stream was stopped and stream of ozone was passed until blue color appeared. The solution was purged with oxygen until blue color disappeared and treated with NaBH$_4$ (1.2 g; 32 mmol). After 20 min. the second portion of NaBH$_4$ (1.2 g; 32 mmol) was added and reaction was allowed to warm to room temperature. The third portion of NaBH$_4$ (1.2 g; 32 mmol) was added and reaction mixture was stirred at room temperature overnight. The reaction was quenched with 70 mL of water and concentrated under vacuum. The residue was extracted with methylene chloride (3×100 mL). The organic phase was washed with 1M aqueous solution of HCl (2×100 mL), saturated aqueous solution of NaHCO$_3$ (100 mL), dried over anhydrous MgSO$_4$ and concentrated under vacuum. The residue was purified by flash chromatography (25% ethyl acetate/hexane) to yield 2.05 g (9.69 mmol; 76% yield) of diol 1 as white crystals. [α]$_D$=+ 56.0 (c 0.95, CHCl$_3$); m.p. 110-111° C.; $^1$H NMR (400 MHz, CDCl$_3$) δ 0.96 (3H, s), 1.03 (3H, d, J=6.6 Hz), 3.38 (1H, dd, J=10.5 Hz, J=6.8 Hz), 3.64 (1H, dd, J=10.5 Hz, J=3.2 Hz), 4.09 (1H, d, J=2.3 Hz); $^{13}$C NMR (100 MHz, CDCl$_3$) δ 13.6, 16.6, 17.4, 22.6, 26.6, 33.5, 38.2, 40.2, 41.3, 52.3, 52.9, 67.8, 69.2; MS (EI) m/z 212 (M$^+$, 2), 194 (17), 179 (18), 163 (10), 135 (19), 125 (34), 111 (100); exact mass calculated for C$_{13}$H$_{22}$O ([M−H$_2$O]$^+$) 194.1671. found 194.1665.

Des-A,B-22-(acetoxy)-23,24-dinorcholane-8β-ol (2)

To a stirred solution of 1 (3.50 g, 16.5 mmol) and DMAP (100 mg) in triethylamine (3.00 mL, 1.67 g, 21.6 mmol) and methylene chloride (300 mL) acetic anhydride (1.54 mL, 2.18

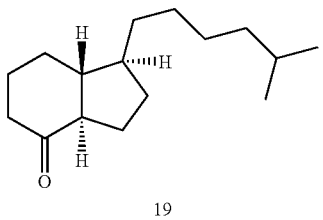

19

Scheme III

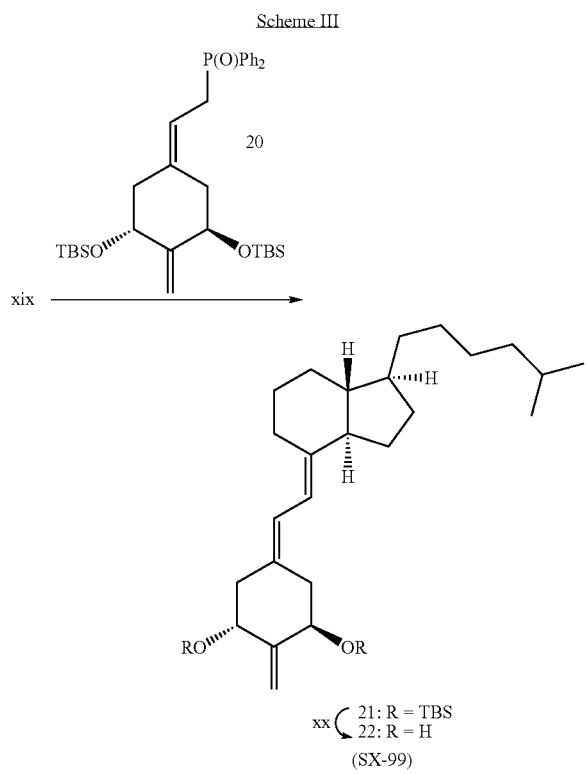

xx { 21: R = TBS
     22: R = H (SX-99)

(i) O$_3$, MeOH, py; NaBH$_4$, 76%. (ii) Ac$_2$O, Et$_3$N, DMAP, CH$_2$Cl$_2$, 97%.
(iii) TESOTf, 2,6-lutidine, CH$_2$Cl$_2$. (iv) MeONa/MeOH, 97% from 2.
(v) SO$_3$/py, DMSO, Et$_3$N, CH$_2$Cl$_2$, 78%. (vi) O$_2$, t-BuOK, t-BuOH, 67%.
(vii) m-CPBA, cyclohexane, 58%. (viii) MeONa/MeOH, MeOH, 90%.
(ix) PDC, PPTS, CH$_2$Cl$_2$, 85%. (x) 10, t-BuOK, THF, 63%. (xi) 5% Pd/C, EtOAc, 93%. (xii) CSA, n-BuOH, 98%. (xiii) t-BuONO, CHCl$_3$.
(xiv) hv, C$_6$H$_6$; i-PrOH, 40% from 13. (xv) Ac$_2$O, 92%. (xvi) MeONa, MeOH, 89%. (xvii) K, HMPA, t-BuOH, Et$_2$O, 80%. (xviii) PDC, PPTS, CH$_2$Cl$_2$, 86%. (xix) 20, PhLi, THF, 40%. (xx) CSA, n-BuOH, 62%.

An overall process for synthesizing 2-alkylidene-19-nor-vitamin D compounds is illustrated and described in U.S. Pat. No. 5,843,928, U.S. Pat. No. 6,627,622, U.S. Pat. No. 6,579,861, U.S. Pat. No. 5,086,191, U.S. Pat. No. 5,585,369, and U.S. Pat. No. 6,537,981, which are hereby incorporated by reference in its entirety and for all purposes as if fully set forth herein.

Compounds of formula I and formula II can be prepared using the methods shown in Schemes I, II and III. For the compound of formula II, the starting material, compound 10, was prepared using known procedures, as shown below in Scheme IV. See also, Andrzej R. Daniewski and Wen Liu, J. Org. Chem. 66, 626-628 (2001), which is hereby incorporated by reference in its entirety and for all purposes as if fully set forth herein.

g, 16.5 mmol) was added dropwise at 0° C. The reaction mixture was kept at 4° C. overnight. Solvents were removed under reduced pressure and the residue was redissolved in methylene chloride (200 mL), washed with 10% aqueous solution of HCl (50 mL), saturated aqueous solution of NaHCO$_3$ (50 mL) and water (50 mL). Organic phase was dried over anhydrous Na$_2$SO$_4$ and concentrated under reduced pressure to give 4.06 g (16.0 mmol; 97% yield) of 2 as white crystals. $[\alpha]_D$=+33.7 (c 0.90), CHCl$_3$); m.p. 78-80° C.; $^1$H NMR (500 MHz, CDCl$_3$) δ 0.96 (3H, s), 1.00 (3H, d, J=6.6 Hz), 2.05 (3H, s), 3.77 (1H, dd, J=10.6 Hz, J=7.7 Hz), 4.06 (1H, dd, J=10.6 Hz, J=3.3 Hz), 4.11 (1H, br s); $^{13}$C NMR (100 MHz, CDCl$_3$) δ 13.5, 17.0, 17.4, 21.0, 22.5, 26.6, 33.5, 35.3, 40.2, 41.9, 52.3, 53.2, 69.1, 69.4, 171.4; MS (EI) m/z 254 (M+, 2), 236 (5), 205 (2), 194 (12), 176 (22), 161 (14), 135 (16), 125 (34), 111 (100); exact mass (ESI) calculated for C$_{15}$H$_{23}$O$_3$Na ([M+Na]$^+$) 277.1780. found 277.1791.

Des-A,B-22-(acetoxy)-8β-[(triethylsilyl)oxy]-23,24-dinorcholane (3)

To a stirred solution of 2 (4.00 g, 16.6 mmol) in methylene chloride (40 mL) and 2,6-lutidine (2.67 mL, 2.46 g, 23.0 mmol) triethylsilyl trifluoromethanesulfonate (4.52 mL, 5.28 g, 20.0 mmol) was added dropwise under argon at −50° C. After 30 min, wet methylene chloride (5 mL) and water (80 mL) were added. The reaction mixture was extracted with methylene chloride (3×120 mL) and organic phase was washed with saturated aqueous solution of CuSO$_4$ (50 mL), dried over anhydrous Na$_2$SO$_4$ and concentrated under reduced pressure to give crude 3 as oil. $[\alpha]^D$=+42.2 (c 1.25, CHCl$_3$); $^1$H NMR (500 MHz, CDCl$_3$) δ 0.55 (6H, q, J=7.9 Hz), 0.93 (3H, s), 0.95 (9H, t, J=8.0 Hz), 0.98 (3H, d, J=6.6 Hz), 2.05 (3H, s), 3.77 (1H, dd, J=10.6 Hz, J=7.5 Hz), 4.04-4.07 (2H, m); $^{13}$C NMR (125 MHz, CDCl$_3$) δ 4.9, 6.9, 13.5, 17.1, 17.6, 21.0, 23.0, 26.8, 34.6, 35.4, 40.6, 42.2, 52.8, 53.4, 69.2, 69.6, 171.4; MS (EI) m/z 368 (M$^+$, 4), 339 (30), 325 (15), 177 (89), 145 (100); exact mass calculated for C$_{21}$H$_{40}$O$_3$Si 368.2747. found 368.2748.

Des-A,B-8β-[(triethylsilyl)oxy]-23,24-dinorcholane-22-ol (4)

To a stirred solution of crude 3 in methanol (100 mL) 10% solution of sodium methanolate in methanol (20 mL) was added dropwise. After 2 h saturated aqueous solution of NH$_4$Cl (20 mL) and water (60 mL) were added and the mixture was extracted with CH$_2$Cl$_2$ (5×100 mL). Organic phase was dried over anhydrous Na$_2$SO$_4$, concentrated under reduced pressure and the residue was purified on silica gel column (10-20% ethyl acetate/hexane) to give 5.25 g (16.1 mmol; 97% yield from 2) of 4. $[\alpha]_D$=+40.3 (c 1.00, CHCl$_3$); $^1$H NMR (400 MHz, CDCl$_3$) δ 0.55 (6H, q, J=7.9 Hz), 0.93-0.97 (12H, m), 1.02 (3H, d, J=6.6 Hz), 3.37 (1H, dd, J=10.4 Hz, J=6.8 Hz), 3.63 (1H, dd, J=10 Hz, J=3.0 Hz), 4.04 (1H, d, J=1.8 Hz); $^{13}$C NMR (100 MHz, CDCl$_3$) δ 4.9, 6.9, 13.6, 16.6, 17.6, 23.0, 26.8, 34.6, 38.3, 40.6, 42.1, 52.8, 53.1, 68.0, 69.3; MS (EI) m/z 326 (M$^+$, 10), 311 (2), 297 (93), 283 (36), 225 (16), 193 (21), 177 (100); exact mass calculated for Cl$_{19}$H$_{38}$O$_2$Si 326.2641. found 326.2639.

Des-A,B-8β-[(triethylsilyl)oxy]-23,24-dinorcholane-22-al (5)

Sulfur trioxide pyridine complex (7.42 g, 46.5 mmol) was added to the stirred solution of 4 (2.32 g, 7.02 mmol) in triethylamine (5.46 mL, 3.94 g, 39.0 mmol), anhydrous DMSO (8.0 mL) and anhydrous CH$_2$Cl$_2$ (40 mL) at 0° C. under argon. After 20 min. methylene chloride (150 mL) was added and reaction mixture was washed with saturated aqueous solution of CuSO$_4$ (40 mL) and water (40 mL). Organic phase was dried over anhydrous Na$_2$SO$_4$, concentrated under reduced pressure and residue was purified on silica gel (0.5-2% ethyl acetate/hexane) to give 1.80 mg (5.56 mmol; 78% yield) of 5. $[\alpha]_D$=+42.6 (c 1.15, CHCl$_3$); $^1$H NMR (400 MHz, CDCl$_3$) δ 0.57 (6H, q, J=7.9 Hz), 0.94-0.98 (12H, m), 1.10 (3H, d, J=6.8 Hz), 2.35 (1H, m), 4.07 (1H, d, J=2.5 Hz), 9.58 (1H, d, J=3.2 Hz); $^{13}$C NMR (100 MHz, CDCl$_3$) δ 5.0, 6.9, 13.4, 13.9, 17.6, 23.3, 26.2, 34.6, 40.6, 42.7, 49.1, 51.8, 52.5, 53.2, 69.1, 205.3; MS (EI) m/z 324 (M$^+$, 4), 311 (12), 295 (100); exact mass calculated for C$_{17}$H$_{31}$O$_2$Si ([M−C$_2$H$_5$]$^+$) 295.2093. found 295.2086.

Des-A,B-8β-[(triethylsilyl)oxy]-pregnane-20-one (6)

Through a solution of potassium tert-butanolate (3.7 g; 33 mmol) in tert-butanol (90 mL) oxygen was passed for 15 min. Then a solution of 5 in tert-butanol (45 mL) was added dropwise while purging with oxygen. Saturated aqueous solution of NH$_4$Cl (80 mL) and water (50 mL) were added and the reaction products were extracted with Et$_2$O (5×150 mL). Organic phase was dried over anhydrous MgSO$_4$, concentrated under reduced pressure and the residue was purified by column chromatography (3-6% ethyl acetate/hexane) to give 1.14 g (3.68 mmol; 67% yield) of 6. $[\alpha]_D$=+107.1 (c 0.80, CHCl$_3$); $^1$H NMR (400 MHz, CDCl$_3$) δ 0.55 (6H, q, J=7.9 Hz), 0.85 (3H, s), 0.94 (9H, t, J=7.9 Hz), 2.09 (3H, s), 2.47 (1H, t, J=9.0 Hz), 4.07 (1H, d, J=2.3 Hz); $^{13}$C NMR (100 MHz, CDCl$_3$) δ 4.9, 6.9, 15.3, 17.6, 21.8, 23.1, 31.5, 34.4, 39.9, 43.7, 53.3, 64.5, 68.9, 209.5; MS (EI) m/z 310 (M$^+$, 50), 281 (84), 211 (73), 173 (94), 87 (100); exact mass calculated for C$_{18}$H$_{34}$O$_2$Si 310.2328. found 310.2332.

Des-A,B-8β-[(triethylsilyl)oxy]-testosterone acetate (7)

To a stirred solution of 6 in cyclohexane (50 mL) meta-chloroperbenzoic acid (77% max.; 1.5 g) was added at 0° C. Then the reaction mixture was warmed up to room temperature and stirred for 5 days. Next portions of meta-chloroperbenzoic acid (1.0 g, 0.8 g and 0.6 g) were added after 1 day, 2 days and 4 days, respectively. The suspension was filtered off and the filtrate was washed with saturated aqueous solution of NaHCO$_3$ (20 mL). Organic phase was dried over anhydrous MgSO$_4$, concentrated under reduced pressure and the residue was purified by column chromatography (1-3% ethyl acetate/hexane) to give 0.89 g (2.73 mmol; 58% yield) of 7. $[\alpha]_D$=+18.7 (c 0.9, CHCl$_3$); $^1$H NMR (400 MHz, CDCl$_3$) δ 0.56 (6H, q, J=7.9 Hz), 0.95 (9H, t, J=7.9 Hz), 1.11 (3H, s), 2.03 (3H, s), 4.05 (1H, d, J=2.0 Hz); $^{13}$C NMR (100 MHz, CDCl$_3$) δ 4.9, 6.9, 13.6, 17.2, 21.2, 22.2, 26.7, 34.5, 37.8, 42.0, 47.8, 69.0, 82.9, 171.3; MS (EI) m/z 326 (M$^+$, 3), 297 (18), 283 (8), 145 (70), 135 (100); exact mass calculated for C$_{18}$H$_{34}$O$_3$Si 326.2277. found 326.2269.

Des-A,B-8β-[(triethylsilyl)oxy]-testosterone (8)

7 (972 mg; 2.98 mmol) was dissolved in methanol (25 ml) and treated with 10% solution of sodium methoxide in methanol (5 mL) for 2.5 h. Saturated aqueous solution of NH$_4$Cl (10 mL) and water (15 mL) were added and product was extracted with methylene dichloride (5×75 mL). Organic phase was dried over anhydrous MgSO$_4$, concentrated under reduced pressure and the residue was purified by column chromatography (5-15% ethyl acetate/hexane) to give 764 mg (2.69 mmol; 90% yield) of 8. $[\alpha]_D$=+39.6 (c 0.95, CHCl$_3$); m.p. 95° C.; $^1$H NMR (400 MHz, CDCl$_3$) δ 0.56 (6H, q, J=7.9 Hz), 0.95 (9H, t, J=7.9 Hz), 0.96 (3H, s), 3.56 (1H, m), 4.02 (1H, d, J=2.4 Hz); $^{13}$C NMR (100 MHz, CDCl$_3$) δ 5.0, 6.9, 12.4, 17.3, 22.2, 29.9, 34.6, 37.5, 42.2, 48.1, 69.1, 82.2; MS (EI) m/z 284 (M$^+$, 9), 255 (100), 237 (40), 135 (42), 103 (66); exact mass calculated for C$_{14}$H$_{27}$O$_2$Si ([M–C$_2$H$_5$]$^+$) 255.1780. found 255.1770.

Des-A,B-8β-[(triethylsilyl)oxy]-androstane-17-one (9)

To a stirred solution of 8 (760 mg; 2.68 mmol) and PPTS (30 mg; 0.12 mmol) in methylene dichloride (90 mL) PDC (2.25 g; 5.98 mmol) was added at 0° C. Cooling bath was removed and the reaction mixture was stirred for 9 h. Then solvent was removed under reduced pressure and the residue was purified by column chromatography (5-10% ethyl acetate/hexane) to give 642 mg (2.28 mmol; 85% yield) of 9. $[\alpha]_D$=+82.9 (c 0.90, CHCl$_3$); $^1$H NMR (500 MHz, CDCl$_3$) δ 0.60 (6H, q, J=7.9 Hz), 0.97 (9H, t, J=7.9 Hz), 1.11 (3H, s), 2.43-2.47 (1H, m), 4.19 (1H, m); $^{13}$C NMR (125 MHz, CDCl$_3$) δ 4.9, 6.9, 16.3, 17.0, 21.3, 32.3, 34.5, 35.3, 47.5, 48.8, 69.9, 221.2; MS (EI) m/z 282 (M$^+$, 10), 252 (100), 133 (17), 103 (39); exact mass calculated for C$_{16}$H$_{30}$O$_2$Si 282.2015. found 282.2013.

(17Z)-Des-A,B-8β-[(triethylsilyl)oxy]-21-norcholest-17-ene (11)

To a stirred suspension of 10 (4.10 g; 9.35 mmol) in THF (13.5 mL) 1M solution of potassium tert-butoxide in THF (8.90 mL; 8.90 mmol) was added dropwise at –10° C. The suspension was stirred and warmed up to 0° C. over 30 min. Then a solution of 9 (716 mg; 2.53 mmol) in THF (3.0 mL) was added via cannula and the resulting mixture was stirred at 45° C. for 4 days. Then saturated aqueous solution of NH$_4$Cl (20 mL) and water (30 mL) were added and the mixture was extracted with diethyl ether (3×100 mL). Organic phase was dried over anhydrous MgSO$_4$, concentrated under reduced pressure and the residue was purified by column chromatography (hexane-5% ethyl acetate/hexane) to give 572 mg (1.60 mmol; 63% yield) of 11 (Z/E ratio 5:1). $[\alpha]_D$=+4.1 (c 0.95, CHCl$_3$); $^1$H NMR (600 MHz, CDCl$_3$) δ 0.56 (6H, q, J=7.9 Hz), 0.86 (6H, d, J=6.7 Hz), 0.95 (9H, t, J=7.9 Hz), 1.10 (3H, s), 4.11 (1H, s), 4.94 (0.83, t, J=7.3 Hz), 5.36 (0.17H, t, J=4.7 Hz); $^{13}$C NMR (100 MHz, CDCl$_3$) δ 5.0, 7.0, 18.0, 19.9, 22.6, 22.7, 23.8, 27.5, 27.6, 27.7, 28.0, 28.7, 30.6, 34.6, 38.3, 38.7, 38.9, 44.2, 52.8, 69.7, 119.3, 130.0, 149.9; MS (EI) m/z 364 (M$^+$, 6), 335, (23), 321 (10), 279 (37), 232 (54), 205 (43), 171 (51), 147 (100); exact mass calculated for C$_{23}$H$_{44}$OSi 364.3161. found 364.3175.

Des-A,B-8β-[(triethylsilyl)oxy]-21-norcholestane (12)

A stirred mixture of 11 (552 mg; 1.52 mmol) and 5% Pd/C (160 mg) in ethyl acetate (20 mL) was treated with hydrogen overnight. The the catalyst was filtered off and the filtrate was concentrated under reduced pressure. The residue was purified on silica gel Sep-Pack cartridge (hexane) to give 515 mg (1.41 mmol; 93% yield) of 12. $[\alpha]_D$=+41.8 (c 1.15, CHCl$_3$); $^1$H NMR (400 MHz, CDCl$_3$) δ 0.55 (6H, q, J=7.9 Hz), 0.81 (3H, s), 0.86 (6H, d, J=6.6 Hz), 0.95 (9H, t, J=7.9 Hz), 4.05 (1H, m); $^{13}$C NMR (100 MHz, CDCl$_3$) δ 5.0, 7.0, 14.1, 17.6, 22.7, 22.7, 23.4, 27.8, 28.0, 29.1, 30.0, 35.0, 38.9, 39.1, 41.5, 51.7, 52.8, 69.2; MS (EI) m/z 337 (100), 323 (59), 271 (67), 233 (77); exact mass calculated for C$_{21}$H$_{41}$OSi ([M–C$_2$H$_5$]$^+$) 337.2927. found 337.2911.

Des-A,B-21-norcholestane-8β-ol (13)

To a stirred solution of 12 (485 mg; 1.33 mmol) in n-butanol (25 mL) (1S)-(+)-10-camphorsulfonic acid (330 mg; 1.42 mmol). After 1 day solvent was removed under reduced pressure and the residue was purified by column chromatography (5-15% ethyl acetate/hexane) to give 328 mg (1.30 mmol; 98% yield) of 13. $[\alpha]_D$=+34.1 (c 1.25, CHCl$_3$); $^1$H NMR (400 MHz, CDCl$_3$) δ 0.84 (3H, s), 0.86 (6H, d, J=6.6 Hz), 4.10 (1H, br s); $^{13}$C NMR (100 MHz, CDCl$_3$) δ 14.0, 17.4, 22.7, 22.7, 22.9, 27.6, 28.0, 28.0, 29.0, 29.9, 33.9, 38.5, 39.1, 41.3, 51.5, 52.3, 69.3; MS (EI) m/z 252 (M$^+$, 43), 237 (44), 219 (22), 209 (19), 125 (49), 111 (100); exact mass calculated for C$_{17}$H$_{32}$O 252.2453. found 252.2446.

Des-A,B-21-norcholestane-8β-yl nitrite (14)

To a stirred solution of 13 (275 mg, 1.09 mmol) in chloroform (5 mL) tert-butyl nitrite (1.5 mL) was added dropwise in darkness. After 1 h benzene was added and solvents were removed under reduced pressure.

(18E)-18-(Hydroxyimino)-des-A,B-21-norcholestane-8β-ol (15)

Crude 14 was dissolved in anhydrous benzene (150 mL) and irradiated in an apparatus consisting of a Pyrex vessel with a watercooled immersion well and Hanovia high-pressure mercury arc lamp equipped with Pyrex filter. A slow stream of argon was passed through solution and temperature was maintained at about 10° C. A reaction progress was monitored by TLC. After 30 min. reaction was completed. Benzene was removed under reduced pressure and the residue was dissolved in 2-propanol (5 mL) and kept overnight to accomplish isomerisation of a nitroso compound to an oxime. The solvent was evaporated and the residue was purified on Waters silica gel Sep-Pack cartridge (15-25% ethyl acetate/hexane) to give 122 mg (0.43 mmol, 40% yield starting from 13) of 15. $[\alpha]_D$=+35.5 (c 0.90, CHCl$_3$); $^1$H NMR (400 MHz, CDCl$_3$) δ 0.86 (6H, d, J=6.6 Hz), 4.06 (1H, m), 6.81 (1H, br s), 7.23 (1H, s), 10.91 (1H, s); $^{13}$C NMR (100 MHz, CDCl$_3$) δ 17.3, 22.0, 22.6, 22.6, 27.7, 27.9, 28.1, 29.1, 34.4, 34.6, 38.9, 49.1, 51.8, 52.0, 67.4, 152.4; MS (EI) m/z 281 (M$^+$, 11), 264 (72), 246 (57), 205 (49), 183 (100); exact mass calculated for C$_{17}$H$_{30}$NO ([M–OH]$^+$) 264.2327. found 264.2326.

8β-(Acetoxy)-des-A,B-21-norcholestane-18-nitrile (16)

A solution of 15 (120 mg, 0.43 mmol) in acetic anhydride (7 mL) was refluxed for 1.5 h. The reaction mixture was cooled, poured carefully into ice and extracted with benzene (3×40 mL). Combined organic phases were washed with saturated aqueous solution of NaHCO$_3$ (2×30 mL), water (15 mL), dried over anhydrous Na$_2$SO$_4$ and evaporated. The residue was purified on Waters silica gel Sep-Pack cartridge (3-5% ethyl acetate/hexane) to give 121 mg (0.40 mmol, 92% yield) of 16. $[\alpha]_D$+5.2 (c 1.30, CHCl$_3$); $^1$H NMR (400 MHz, CDCl$_3$) δ 0.86 (6H, d, J=6.6 Hz), 2.13 (3H, s), 2.25-2.28 (1H, m), 5.21 (1H, s); $^{13}$C NMR (100 MHz, CDCl$_3$) δ 18.5, 20.9, 22.6, 23.3, 27.2, 27.6, 27.9, 28.2, 30.1, 30.8, 34.0, 38.9, 46.5, 49.1, 51.2, 68.4, 121.4, 170.9; 20.9, 22.3, 23.4, 27.4, 29.8, 32.1, 36.2, 45.7, 51.9, 56.2, 68.6, 121.1, 170.9; MS (EI) m/z 305 (M+, 7), 288 (3), 263 (83), 245 (44), 220 (79), 205 (100); exact mass (ESI) calculated for $C_{19}H_{31}NO_2Na$ 328.2252. found 328.2249.

Des-A,B-21-norcholestane-18-nitrile-8β-ol (17)

16 (120 mg, 0.39 mmol) was dissolved in methanol (3 mL) and treated with 10% solution of MeONa in methanol (3 mL) for 2 h. After that solvent was removed under reduced pressure, the residue was treated water (10 mL) and saturated aqueous solution of $NH_4Cl$ (8 mL) and extracted with methylene dichloride (3×25 mL). Organic phase was dried over anhydrous $Na_2SO_4$ and evaporated. The residue was purified on Waters silica gel Sep-Pack cartridge (15-25% ethyl acetate/hexane) to give 91 mg (0.35 mmol, 89% yield) of 17. $[α]_D$=+23.0 (c 1.10, $CHCl_3$); $^1H$ NMR (400 MHz, $CDCl_3$) δ 0.86 (6H, d, J=6.6 Hz), 2.24 (1H, d, J=13.0 Hz), 4.12 (1H, m); $^{13}C$ NMR (100 MHz, $CDCl_3$) δ 17.8, 22.6, 22.9, 27.3, 27.6, 27.9, 28.3, 30.7, 33.0, 34.2, 38.9, 45.7, 49.0, 52.6, 67.2, 122.5; MS (EI) m/z 263 (M+, 64), 246 (39), 236 (77), 220 (92), 206 (84), 193 (95), 134 (100); exact mass calculated for $C_{17}H_{29}NO$ 263.2249. found 263.2256.

Des-A,B-18,21-dinorcholestane-8β-ol (18)

To a stirred mixture of potassium (90 mg, 2.31 mmol) in HMPA (350 μL, 361 mg, 2.01 mmol) and diethyl ether (800 μL) the solution of 17 (90 mg, 0.34 mmol) in tert-butyl alcohol (80 μL) and diethyl ether (300 μL) was added dropwise at 0° C. under argon. The mixture was allowed to warm up to room temperature and stirred overnight. Remaining potassium was removed, a few drops of 2-propanol and benzene (20 mL) were added. Organic phase was washed with water (5 mL), dried over anhydrous $Na_2SO_4$ and concentrated under reduced pressure. The residue was purified on Waters silica gel Sep-Pack cartridge (5-15% ethyl acetate/hexane) to give 65 mg (0.27 mmol, 80% yield) of 18. $[α]_D$=+66.8 (c 1.00, $CHCl_3$); $^1H$ NMR (400 MHz, $CDCl_3$) δ 0.86 (6H, d, J=6.6 Hz), 4.04 (1H, s); $^{13}C$ NMR (100 MHz, $CDCl_3$) δ 20.2, 22.6, 22.6, 24.4, 27.7, 27.9, 28.6, 29.2, 30.6, 33.5, 34.4, 39.0, 43.6, 44.6, 50.3, 67.8; MS (EI) m/z 238 (M+, 50), 220 (76), 205 (41), 195 (79), 135 (82), 122 (86), 93 (100); exact mass calculated for $C_{16}H_{30}O$ 238.2297. found 238.2323.

Des-A,B-18,21-dinorcholestane-8-one (19)

To a stirred solution of 18 (7 mg; 29 μmol) and PPTS (2 crystals) in methylene dichloride (2 mL) PDC (40 mg; 105 μmol) was added at 0° C. Cooling bath was removed and the mixture was stirred for 3 h. Then solvent was removed under reduced pressure and the residue was purified on silica gel Sep-Pack cartridge (2-5% ethyl acetate/hexane) to give 6 mg (25 μmol; 86% yield) of 19. $^1H$ NMR (400 MHz, $CDCl_3$) δ 0.86 (6H, d, J=6.6 Hz); $^{13}C$ NMR (100 MHz, $CDCl_3$) δ 21.1, 22.6, 22.7, 27.7, 27.8, 28.0, 28.4, 29.1, 29.6, 34.2, 39.0, 41.5, 45.8, 54.8, 58.1, 211.7; MS (EI) m/z 236 (M+, 69), 220 (31), 205 (100), 193 (67), 138 (61), 121 (94); exact mass calculated for $C_{16}H_{28}O$ 236.2140. found 236.2136.

2-Methylene-1α-hydroxy-18,19,21-trinorvitamin $D_3$(SX-99) (22)

To a stirred solution of 20 (20 mg; 35 μmol) in THF (500 μL) 2 drops of 1.8 M solution of PhLi in di-n-butyl ether was added at −20° C. until the solution became deep orange. Then 17 μL (32 μmol) of the solution of PhLi was added dropwise. After 20 min. the reaction mixture was cooled down to −78° C. and the solution of 19 (5 mg; 21 μmol) in THF (200 μL) was added via cannula. After 3 h hexane (15 mL) was added and organic phase was washed with brine (3 mL), dried over anhydrous $MgSO_4$ and concentrated under reduced pressure. The residue was purified on silica gel Sep-Pack cartridge (hexane-3% ethyl acetate/hexane) to give 5 mg (8 μmol; 40% yield) of 21. $^1H$ NMR (400 MHz, $CDCl_3$) δ 0.03 (3H, s), 0.04 (3H, s), 0.07 (3H, s), 0.08 (3H, s), 0.86-0.87 (15H, m), 0.89 (9H, s), 2.18 (1H, dd, J=12.4 Hz, J=7.8 Hz), 2.38-2.49 (3H, m), 2.86 (1H, d, J=13.6 Hz), 4.42 (2H, m), 4.93 (1H, s), 4.96 (1H, s), 5.92 (1H, d, J=11.1 Hz), 6.19 (1H, d, J=11.1 Hz); MS (EI) m/z 468 (77), 366 (55), 234 (32), 220 (42), 205 (63), 73 (100); exact mass calculated for $C_{31}H_{52}OSi$ ([M−t-BuSi $(Me)_2$ O—H]+) 468.3787. found 468.3785.

To a stirred solution of 21 (4 mg; 6.5 μmol) in ethanol (500 μL) (1S)-(+)-10-camphorsulfonic acid (3 mg; 13 μmol) was added at 0° C. Then cooling bath was removed and the reaction mixture was stirred for 3 days. A few drops of saturated aqueous solution of $NaHCO_3$ and water (2 mL) were added and the mixture was extracted with ethyl acetate (5×7 mL). Combined organic phases were dried over anhydrous $MgSO_4$, concentrated under reduced pressure and the residue was purified on silica gel Sep-Pack cartridge (15-25% ethyl acetate/hexane) to give ca. 2.5 mg of crude 22. The crude vitamin was purified on HPLC (10% isopropanol/hexane; 10 mm×25 cm Zorbax-Sil column; 4 mL/min.; $R_t$=6.56 min. and 5% water/methanol; 9.4 mm×25 cm, 5 □m, Zorbax Eclipse XDB-C18 column; 4 mL/min.; $R_t$=9.74 min.) to give 1.5 mg (4 μmol; 62% yield) of 22. UV (EtOH) $λ_{max}$=243, 251, 260 nm; $^1H$ NMR (400 MHz, $CDCl_3$) δ 0.86 (6H, d, J=6.6 Hz), 2.29-2.37 (2H, m), 2.58 (1H, dd, J=13.2 Hz, J=3.7 Hz), 2.79-2.88 (2H, m), 4.48 (2H, m), 5.09 (1H, s), 5.11 (1H, s, 5.97 (1H, d, J=11.3 Hz), 6.35 (1H, d, J=11.3 Hz); MS (EI) m/z 372 (M+, 91), 354 (10), 287 (100), 219 (53), 107 (51); exact mass calculated for $C_{25}H_{40}O$ 372.3028. found 372.3046.

Toluene-4-sulfonic acid 5-methyl-hexyl ester (23)

To a stirred solution of 5-methyl-1-hexanol (3.65 mL; 3.00 g; 25.7 mmol), triethylamine (5.00 mL; 3.64 g; 36.0 mmol) and DMAP (200 mg; 1.64 mmol) in methylene dichloride (120 mL) tosyl chloride (5.72 g; 30.0 mmol) was added at 0° C. Then cooling bath was removed and the mixture was allowed to stand overnight. Saturated aqueous solution of $NH_4Cl$ (30 mL) and water (30 mL) were added and the mixture was extracted with methylene dichloride (3×150 mL). Combined organic phases were dried over anhydrous $MgSO_4$ and concentrated under reduced pressure. The residue was purified by column chromatography (5-10% ethyl acetate/hexane) to give 6.66 g (24.7 mmol; 96% yield) of 27. $^1H$ NMR (400 MHz, $CDCl_3$) δ 0.83 (6H, d, J=6.6 Hz), 1.09 (2H, m), 1.28 (2H, m), 1.47 (1H, m), 1.62 (2H, m), 2.45 (3H, s), 4.02 (2H, t, J=6.5 Hz), 7.34 (2H, d, J=8.1 Hz), 7.79 (2H, d, J=8.1 Hz); $^{13}C$ NMR (100 MHz, $CDCl_3$) δ 21.6, 22.5, 23.2, 27.8, 29.1, 38.2, 70.2, 127.9, 129.8, 133.2, 144.6; MS (EI) m/z 255 (2), 226 (2), 205 (3), 190 (5), 173 (67), 155 (57), 98 (59), 91 (100) exact mass calculated for $C_{13}H_{19}O_3S$ ([M−$CH_3$]+) 255.1055. found 255.1062.

1-Bromo-5-methyl-hexane (24)

To a stirred solution of LiBr (6.26 g; 72.0 mmol) in DMF (40 mL) a solution of 23 (6.60 g; 24.4 mmol) in DMF (6 mL) was added. The resulting mixture was stirred at 45° C. for 3 h. Then water (100 mL) was added and the reaction product was extracted with diethyl ether (5×250 mL). Removal of solvent yielded in 2.40 g (13.4 mmol; 55%) of 24. $^1H$ NMR (400

MHz, CDCl$_3$) δ 0.88 (6H, d, J=6.6 Hz), 1.19 (2H, m), 1.42 (2H, m), 1.54 (1H, m), 1.83 (2H, m), 3.41 (2H, t, J=6.9 Hz); $^{13}$C NMR (100 MHz, CDCl$_3$) δ 22.5, 26.0, 27.8, 33.1, 34.1, 38.0; MS (EI) m/z 179 (M$^+$, 80), 163 (14), 155 (9), 137 (100); exact mass calculated for C$_6$H$_{12}$Br ([M–CH$_3$]$^+$) 163.0122. found 163.0121.

(5-Methylhexyl)triphenylphosphonium bromide (10)

A solution of 24 (2.30 g; 12.8 mmol) and triphenylphosphine (3.70 g; 14.1 mmol) was refluxed in toluene (12 mL) for 20 h. Then solvent was removed and the resulting crystal was washed with toluene (3 mL) and diethyl ether (3 mL) to give 4.57 g (10.4 mmol; 81% yield) of 10. m.p. 227-228° C.; $^1$H NMR (500 MHz, CD$_3$CN) δ 0.82 (6H, d, J=6.6 Hz), 1.16 (2H, m), 1.42-1.52 (3H, m), 1.59 (2H, m), 3.30 (2H, m), 7.72 (12H, m), 7.85 (3H, m); $^{13}$C NMR (125 MHz, CD$_3$CN) δ 22.7, 23.2, 28.4, 28.8, 28.9, 38.6, 131.2, 131.3, 134.7, 134.7, 136.0.

Example II

Biological Activity (A) Vitamin D Receptor Binding
Test Material
Protein Source

Full-length recombinant rat receptor was expressed in *E. coli* BL21(DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at –80° C. until use. For use in binding assays, the protein was diluted in TEDK$_{50}$ (50 mM Tris, 1.5 mM EDTA, pH7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry (1,25 (OH)$_2$D$_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25(OH)$_2$D$_3$, ~159 Ci/mmole) was added in ethanol at a final concentration of 1 nM.

Assay Conditions

Radiolabeled and unlabeled ligands were added to 100 mcl of the diluted protein at a final ethanol concentration of <10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

(B) HL-60 Differentiation
Test Material
Study Drugs

The study drugs were dissolved in ethanol and the concentrations determined using UV spectrophotometry. Serial dilutions were prepared so that a range of drug concentrations could be tested without changing the final concentration of ethanol (<0.2%) present in the cell cultures.

Cells

Human promyelocytic leukemia (HL60) cells were grown in RPMI-1640 medium containing 10% fetal bovine serum. The cells were incubated at 37° C. in the presence of 5% CO$_2$.

Assay Conditions

HL60 cells were plated at 1.2×10$^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

(C) In vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer. (RLU=relative luciferase units)

(D) Intestinal Calcium Transport and Bone Calcium Mobilization

Male, weanling Sprague-Dawley rats were placed on Diet 11 (0.47% Ca) diet+AEK for one week followed by Diet 11 (0.02% Ca)+AEK for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method. The everted gut sac assay was carried out as previously described by Martin and Deluca, Am. J. Physiol. 216, 1351 (1969); (DeLuca et al., U.S. Pat. No. 4,188,345), which are incorporated by reference as if fully set forth herein.

Dose Preparation
Control Material
A. Negative Control Material

The negative control material is prepared by volumetrically measuring ethanol (<5%) and propylene glycol, mixing, and then placing in storage at 2 to 8° C.

B. Positive Control Material 1,25 OH)$_2$D$_3$ is prepared by determining the concentration of an ethanol stock solution using UV spectrophotometry (extinction coefficient=18,200; λmax=265 nm). The required amount of 1,25(OH)$_2$D$_3$ is volumetrically measured into propylene glycol so that there was less than 5% ethanol in the final solution. The solution is mixed and then stored at 2 to 8° C.

Test Material

The analogs are prepared by first determining the concentration of an ethanol stock solution using UV spectrophotometry (extinction coefficient=42,000; $\lambda_{max}$=252 nm). The analog solutions are then volumetrically added to propylene glycol so that there was less than 5% ethanol in the final solution. The solution is mixed and stored at 2 to 8° C.

Dose Administration Method

Both control and test articles are administered by intraperitoneal injection in 100 microliters for 4-7 consecutive days spaced approximately 24 hours apart. $1,25(OH)_2D_3$ is given for 4 consecutive days, whereas, the test drugs are given for 7 consecutive days.

Serum Calcium Analysis

Twenty-four hours after the final dose, approximately 1 ml of blood is allowed to coagulate at room temperature and then centrifuged at 3000×g for 15 minutes. The serum is transferred to a polypropylene tube and stored frozen at −20° C. The level of calcium is determined by diluting the serum into 0.1% lanthum chloride and measuring the absorbance on an atomic absorption spectrophotometer (Perkin Elmer Model 3110, Shelton, Conn.).

Figure 2:
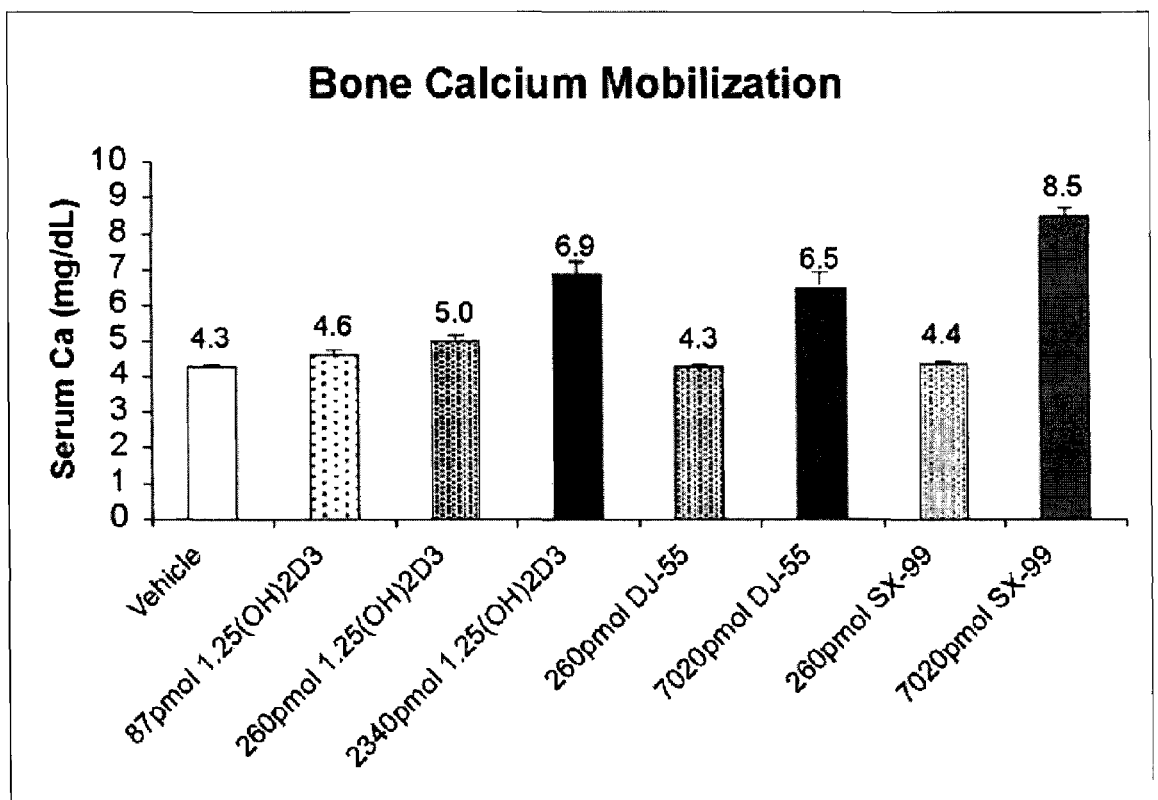
Figure 3:
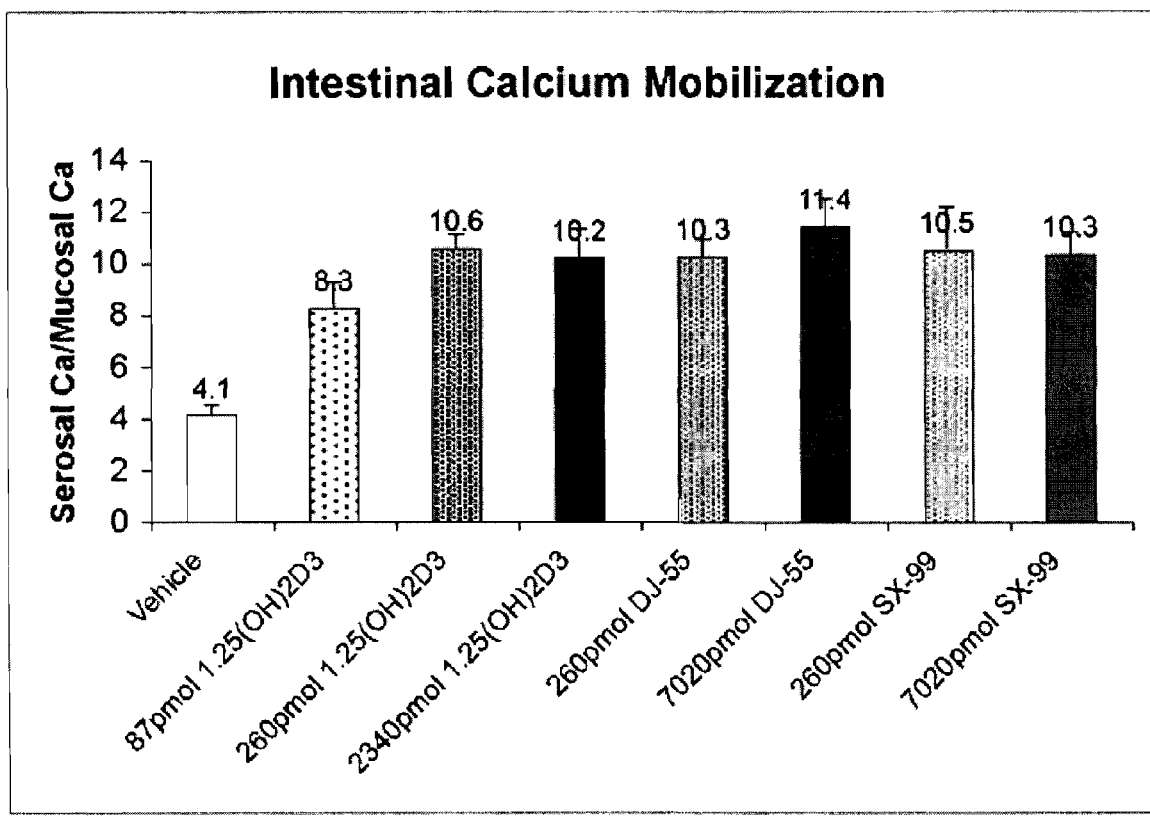
Figure 4:
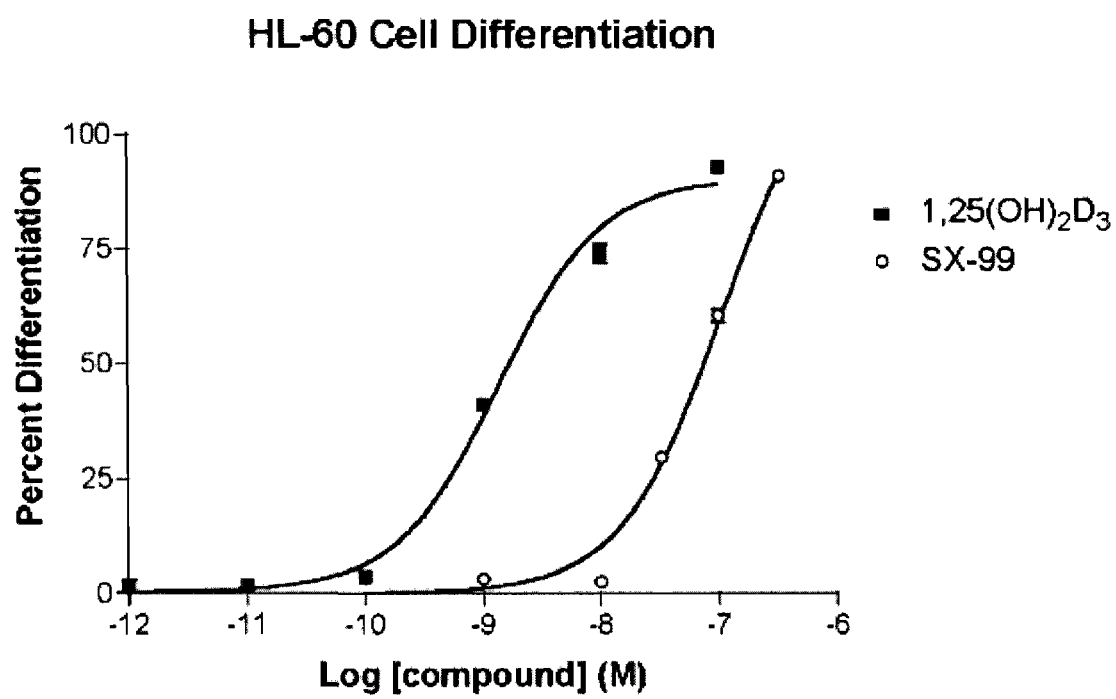
Figure 5:
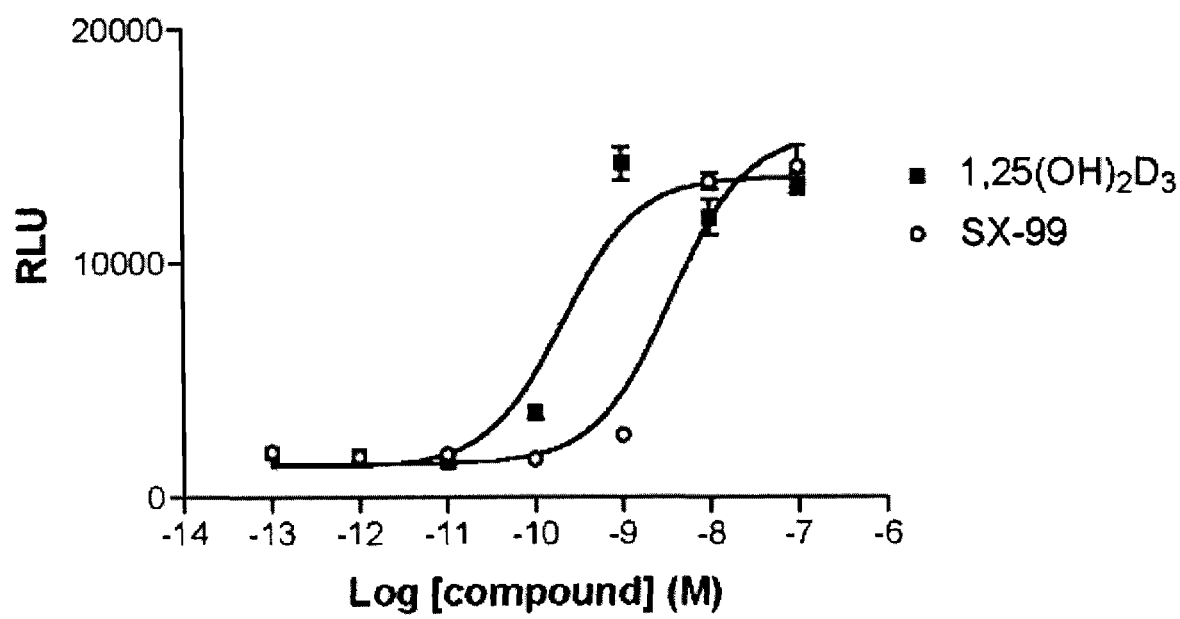

2-Methylene-1α-hydroxy-18,19,21-trinorvitamin D3 (SX-99) binds to the recombinant vitamin D receptor, and is considerably less active when compared to 1α,25-dihydroxyvitamin $D_3$ in this respect (see FIG. 1). Additionally, it is also less active in stimulating transcription of a reporter gene stably transfected in Ros17/2.8 (bone) cells. In vivo, this compound would be expected to be hydroxylated in the liver to produce the 1α,25-dihydroxyvitamin $D_3$ compound which would then be able to bind tightly to the receptor and carry out transcription (see FIG. 5). It is slightly less active as 1α,25-dihydroxyvitamin $D_3$ in inducing differentiation of HL-60 cells (see FIG. 4). It has significant bone calcium mobilization activity and potent calcium transport activity in vivo (see FIGS. 2 and 3). Accordingly, SX-99 is expected to possess significant activity in suppressing parathyroid hormone levels in normal rats.

Similarly, other similar compounds of the present invention as shown in formula I or II, are expected to bind to the vitamin D receptor, stimulate transcription of a reporter gene stably transfected in Ros17/2.8 (bone) cells, induce differentiation of HL-60 cells, have significant calcemic activity when measured either by intestinal calcium transport or bone calcium mobilization than 1α,25-dihydroxyvitamin $D_3$ and possess significant activity in suppressing parathyroid hormone levels in normal rats.

Accordingly, this compound SX-99 and other compounds described in the invention should find its uses in the treatment of autoimmune diseases such as multiple sclerosis, type I diabetes, rheumatoid arthritis, lupus, and other similar degenerative diseases. It should also have significant activity in treating malignant growth such as colorectal, breast, skin, lung and prostate cancers. This compound should also be useful in treating secondary hyperparathyroidism found in patients who have lost kidney function such as those on hemodialysis or peritoneal dialysis. Its significant calcemic activity should make it useful in the treatment of osteopenia, and metabolic bone diseases such as osteomalacia, vitamin D resistant rickets and osteoporosis particularly senile osteoporosis, postmenopausal osteoporosis, steroid-induced osteoporosis and low bone turnover osteoporosis.

In one embodiment, the compounds of formula I are used in a pharmaceutical composition. For example, each ml of the pharmaceutical composition may comprise 5 µg of the compound, 30% (v/v) propylene glycol and 20% (v/v) alcohol.

The compounds of the invention are also useful in preventing or treating obesity, inhibiting adipocyte differentiations, inhibiting SCD-1 gene transcription, and/or reducing body fat in animal subjects. Therefore, in some embodiments, a method of preventing or treating obesity, inhibiting adipocyte differentiations, inhibiting SCD-1 gene transcription, and or reducing body fat in animal subject includes administering to the animal subject, an effective amount of the compound or a pharmaceutical composition that includes the compound. Administration of the compound or the pharmaceutical composition to the subject inhibits adipocyte differentiation, inhibits gene transcription, and/or reduces body fat in the animal subject.

For treatment purposes, the compounds defined by formula I and formula II are formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically acceptable and non-toxic excipients such as stabilizers, antioxidants, binders, coloring agents or emulsifying or taste-modifying agents. Pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is hereby incorporated by reference in its entirety and for all purposes as if fully set forth herein.

The compounds are administered orally, topically, parenterally, nasally, rectally, sublingually, or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. In some embodiments, doses of from 0.001 µg to about 1 mg per day of the compound are appropriate for treatment purposes. In some such embodiments an appropriate and effective dose may range from 0.01 µg to 1 mg per day of the compound. In other such embodiments an appropriate and effective dose may range from 0.1 µg to 500 µg per day of the compound. Such doses will be adjusted according to the type of disease or condition to be treated, the severity of the disease or condition, and the response of the subject as is well understood in the art. The compound is suitably administered alone, or together with another active vitamin D compound.

In one embodiment, the compound of formula II is used in a pharmaceutical composition. For example, each ml of the pharmaceutical composition may comprise 5 µg of the compound, 30% (v/v) propylene glycol and 20% (v/v) alcohol.

Compositions for use in the invention include an effective amount of 2-methylene-1α-hydroxy-18,19,21-trinorvitamin D3 (SX-99) as the active ingredient, and a suitable carrier. An effective amount of the compound for use in accordance with some embodiments of the invention will generally be a dosage amount such as those described herein, and is administered topically, transdermally, orally, nasally, rectally, sublingually, or parenterally. In one embodiment, the dosage is administered intraperitoneally.

The compounds of formula I or II are advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The compound is formulated as creams, lotions, ointments, aerosols, suppositories, topical patches, pills, capsules or tablets, or in liquid form as solutions, emulsions, dispersions, or suspensions in pharmaceutically innocuous and acceptable solvent or oils, and such preparations may contain, in addition, other pharmaceutically innocuous or beneficial components, such as stabilizers, antioxidants, emulsifiers, coloring agents, binders or taste-modifying agents.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration is in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration is in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100 microns.

The formulations may conveniently be presented in dosage unit form and is prepared by any of the methods well known in the art of pharmacy. By the term "dosage unit" is meant a unitary, i.e., a single dose which is capable of being administered to a patient as a physically and chemically stable unit dose comprising either the active ingredient as such or a mixture of it with solid or liquid pharmaceutical diluents or carriers.

All references cited herein are specifically incorporated by reference in their entireties and for all purposes as if fully set forth herein.

It is understood that the invention is not limited to the embodiments set forth herein for illustration, but embraces all such forms thereof as come within the scope of the following claims.

What is claimed is:

1. A compound having the formula I

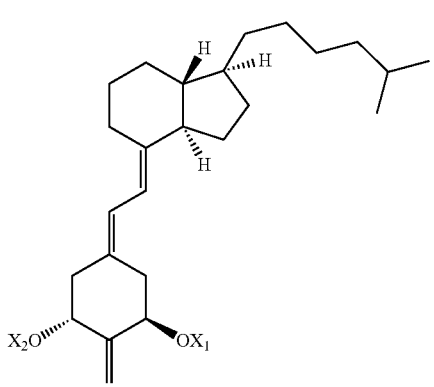

wherein $X_1$ and $X_2$ are independently selected from H and hydroxy protecting groups.

2. The compound of claim 1, wherein $X_1$ and $X_2$ are hydroxy protecting groups.

3. The compound of claim 2, wherein $X_1$ and $X_2$ are triethylsilyl or t-butyldimethylsilyl groups.

4. The compound of claim 1, wherein $X_1$ and $X_2$ are H and the compound has the formula II

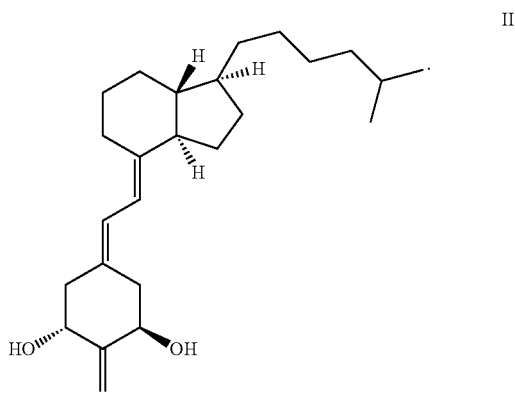 [SMILES: C=C1[C@H](O)CC(=C/C=C2\CCC[C@@H]3[C@@H](CCCCC(C)C)CC[C@@H]23)C[C@H]1O]

5. A pharmaceutical composition, comprising an effective amount of the compound of claim 1 and a pharmaceutically acceptable carrier.

6. The pharmaceutical composition of claim 5 wherein the effective amount comprises from about 0.01 µg to about 1 mg of the compound per gram of the composition.

7. The pharmaceutical composition of claim 5 wherein the effective amount comprises from about 0.1 µg to about 500 µg of the compound per gram of the composition.

8. A method of treating a subject suffering from a biological condition, comprising administering an effective amount of the compound of claim 1 to the subject, wherein the biological condition is selected from metabolic bone disease; psoriasis; leukemia; colon cancer; breast cancer; prostate cancer; skin cancer; lung cancer; multiple sclerosis; lupus; diabetes mellitus; host versus graft reaction; rejection of organ transplants; an inflammatory disease selected from rheumatoid arthritis, asthma, or inflammatory bowel diseases; a skin condition selected from wrinkles, lack of adequate skin firmness, lack of adequate dermal hydration, or insufficient sebum secretion; renal osteodystrophy; osteopenia; or osteoporosis.

9. The method of claim 8, wherein the biological condition is renal osteodystrophy, vitamin D-resistant rickets, osteoporosis or psoriatic arthritis.

10. The method of claim 8, wherein the biological condition is selected from leukemia, colon cancer, breast cancer, skin cancer, lung cancer or prostate cancer.

11. The method of claim 8, wherein the biological condition is selected from multiple sclerosis, lupus, diabetes mellitus, host versus graft reaction, or rejection of organ transplants.

12. The method of claim 8, wherein the biological condition is selected from rheumatoid arthritis, asthma, or inflammatory bowel diseases selected from celiac disease, ulcerative colitis and Crohn's disease.

13. The method of claim 8, wherein the biological condition is selected from wrinkles, lack of adequate skin firmness, lack of adequate dermal hydration, or insufficient sebum secretion.

14. The method of claim 8, wherein the compound is administered orally, parenterally, nasally, rectally, sublingually, transdermally or topically to the subject.

15. The method of claim 8, wherein the compound is administered intraperitoneally.

16. The method of claim 8, wherein the compound is administered in a dosage of from 0.01 µg per day to 1 mg per day.

17. A compound having the formula II

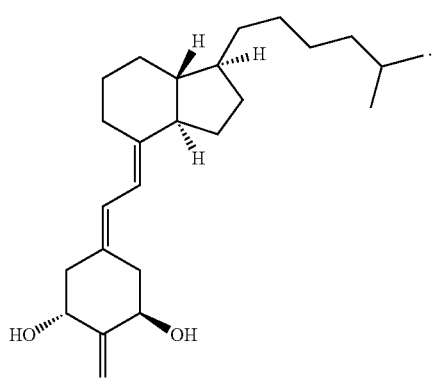

18. A pharmaceutical composition, comprising an effective amount of the compound of claim 17 and a pharmaceutically acceptable carrier.

19. The pharmaceutical composition of claim 18 wherein the effective amount comprises from about 0.01 μg to about 1 mg of the compound per gram of the composition.

20. The pharmaceutical composition of claim 18 wherein the effective amount comprises from about 0.1 μg to about 500 μg of the compound per gram of the composition.

21. A method of treating obesity of an animal, inhibiting adipocyte differentiation, inhibiting SCD-1 gene transcription, and/or reducing body fat in an animal comprising administering to an animal in need thereof an effective amount of a compound having the formula:

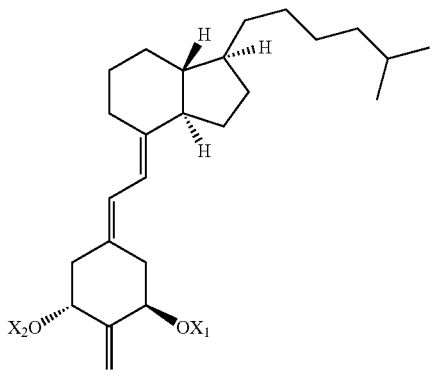

wherein $X_1$ and $X_2$ are independently selected from H and hydroxy protecting groups.

22. The method of claim 21 wherein the compound is administered orally, parenterally nasally, rectally, sublingually, transdermally or topically to the animal.

23. The method of claim 21 wherein the compound is administered in a dosage of from 0.01 μg per day to 1 mg per day.

24. The method of claim 21 wherein the compound is 2-methylene-1α-hydroxy-18,19,21-trinorvitamin D having the formula:

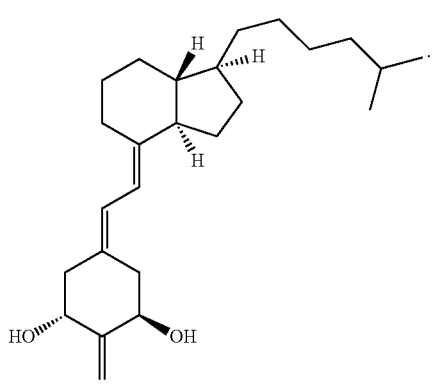

25. The method of claim 21 wherein the animal is a human.

26. The method of claim 21 wherein the animal is a domestic animal.

27. The method of claim 21 wherein the animal is an agricultural an animal.

* * * * *